United States Patent [19]

Mallion et al.

[11] Patent Number: 5,691,349

[45] Date of Patent: Nov. 25, 1997

[54] QUINCLIDINE DERIVATIVES AS SQUALENE SYNTHASE INHIBITORS

[75] Inventors: Keith Blakeney Mallion, Knutsford; George Robert Brown, Wilmslow; Paul Robert Owen, Macclesfield, all of United Kingdom

[73] Assignee: Zeneca Limited, London, United Kingdom

[21] Appl. No.: 379,583

[22] PCT Filed: Aug. 4, 1993

[86] PCT No.: PCT/GB93/01648

§ 371 Date: Jun. 23, 1995

§ 102(e) Date: Jun. 23, 1995

[87] PCT Pub. No.: WO94/03451

PCT Pub. Date: Feb. 17, 1994

[30] Foreign Application Priority Data

Aug. 6, 1992 [GB] United Kingdom ............... 9216721

[51] Int. Cl.[6] ................ A61K 31/46; C07D 453/02
[52] U.S. Cl. .................. 514/305; 546/133; 546/137
[58] Field of Search .................. 514/305; 546/133, 546/137

[56] References Cited

U.S. PATENT DOCUMENTS

| 3,405,134 | 10/1968 | Judd | 546/137 |
|---|---|---|---|
| 3,534,053 | 10/1970 | Sallay et al. | 546/133 |
| 3,586,694 | 6/1971 | Shen et al. | 548/309.4 |
| 3,655,675 | 4/1972 | Carabateas | 546/224 |
| 3,679,690 | 7/1972 | Carabateas | 546/309 |
| 3,725,410 | 4/1973 | Potoski et al. | 544/362 |
| 3,763,168 | 10/1973 | Carabateas | 546/133 |
| 3,857,848 | 12/1974 | Mauverney et al. | 546/133 |
| 4,038,402 | 7/1977 | Kaminka et al. | 514/305 |
| 4,599,344 | 7/1986 | Morgan, Jr. | 514/305 |
| 5,135,935 | 8/1992 | Alberts et al. | 514/305 |
| 5,242,914 | 9/1993 | Kawamoto et al. | 514/210 |
| 5,258,392 | 11/1993 | Wieringa et al. | 514/305 |
| 5,286,864 | 2/1994 | Walther et al. | 546/137 |
| 5,385,912 | 1/1995 | Neuenschwander et al. | 514/305 |

FOREIGN PATENT DOCUMENTS

| 648789 | 11/1991 | Australia. |
|---|---|---|
| 77130/91 | 11/1991 | Australia. |
| 1014958 | 8/1977 | Canada. |
| 0 307 142 | 3/1989 | European Pat. Off.. |
| 0 316 718 | 5/1989 | European Pat. Off.. |
| 0 322 182 | 6/1989 | European Pat. Off.. |
| 0 328 200 | 8/1989 | European Pat. Off.. |
| 0 330 826 | 9/1989 | European Pat. Off.. |
| 0 337 637 | 10/1989 | European Pat. Off.. |
| 0 370 415 | 5/1990 | European Pat. Off.. |
| 0 412 797 | 2/1991 | European Pat. Off.. |
| 0 458 214 | 11/1991 | European Pat. Off.. |
| 0 497 415 | 8/1992 | European Pat. Off.. |
| 2 323 303 | 12/1973 | Germany. |
| 25 02 916 | 11/1975 | Germany. |
| 41 16 582 | 11/1991 | Germany. |
| 1 416 958 | 12/1975 | United Kingdom. |
| 2 169 292 | 7/1986 | United Kingdom. |
| 92 15579 | 9/1992 | WIPO. |
| 93/15073 | 8/1993 | WIPO. |
| 93/16048 | 8/1993 | WIPO. |

OTHER PUBLICATIONS

Ricciardi, F.J. et al, Heterocycles, 1986, 24(4), pp. 971–977.

Hassner, A. et al, Organic Synthesis Based on Name Reactions and Unnamed Reactions, 1994, Elsevier Science Ltd., p. 138.

Dieck, H.A. et al, J. Am. Chem. Soc. 1974, 96(4), pp. 1133–1136.

Bondarenko, V.A. et al, Khim–Farm, Zh. 1978, 12(11), pp. 56–60.

Warawa et al, Quinuclidine Chemistry.2.[1] Synthesis and Antiinflammatory Properties of 2–Substituted Benzhydryl–3–quinuclidinols, J. Med. Chem. 17(5), (1974), 497–501.

Sterling et al, Quaternary and Tertiary Quinuclidine Derivatives as Inhibitors of Choline Uptake, J. Pharm. Sciences, 80(8), (1991), 785–789.

Saunders et al, Novel Quinuclidine–Based Ligands for the Muscarinic Cholinergic Receptor, J. Med. Chem. 33(4), (1990), 1128–1137.

Turchin et al, Stereochemistry Of Quinuclidines Containing A Substituent With Aryl (Heteroaryl) Nuclei At Position Three, Khimiko–farmatsevticheskii Zhurnal, 1986, vol. 20, pp. 65–72.

(List continued on next page.)

*Primary Examiner*—C. Warren Ivy
*Assistant Examiner*—Garth M. Dahlen
*Attorney, Agent, or Firm*—Cushman Darby & Cushman Intellectual Property Group of Pillsbury Madison & Sutro, LLP

[57] ABSTRACT

Quinuclidine derivatives of formula, and their pharmaceutically acceptable salts, in which: $R^1$ is hydrogen or hydroxy; $R^2$ is hydrogen; pr $R^1$ and $R^2$ are joined together so that $CR^1-CR^2$ is a double bond; X is selected from $-CH_2CH_2-$, $-CH=CH-$, $-C\equiv C-$, $-CH_2O-$, $-OCH_2-$, $-CH_2NH-$, $NHCH_2-$, $-CH_2CO-$, $-COCH_2-$, $-CH_2S(O)_n-$ and $-S(O)_nCH_2-$ wherein n is 0, 1 or 2; and AR is phenyl which may be optionally unsubstituted or substituted by one or more substituents such as halogeno, hydroxy, amino, nitro, cyano, carboxy, carbamoyl, alkyl, alkenyl, alkynyl, alkoxy, alkylamino, dialkylamino, N-alkylcarbamoyl, N,N-di-alkylcarbamoyl, alkoxycarbonyl, alkythio, alkylsulphinyl, alkylsulphonyl, halogeno alkyl, alkanoylamino, alkylenedioxy, alkanoyl and oxime derivatives thereof and O-alkyl ethers of said oximes; provided that when X is selected from $-OCH_2-$, $-NHCH_2-$, and $SCH_2-$, $R^1$ is not hydroxy; inhibit squalene synthase and are useful in treating diseases or medical conditions in which inhibition of squalene synthase is desirable. The use of such heterocyclic derivatives in treating conditions such as hypercholesterolemia, and atherosclerosis is referred to as well as novel compounds, processes for their preparation and pharmaceutical compositions containing them.

19 Claims, No Drawings

OTHER PUBLICATIONS

Bondarenko et al, Khim. Farm, 12(11), 1978, pp. 56–60.

Khim. Farm, 7(8), 1973, 20–24.

Ricciardi et al, Facile Synthesis Of Styrylquinuclidines, Heterocycles, 24, (1986), pp. 971–977.

Khim, Geterosikl Soedin, 3, (1983), 381–385.

Mikhlina et al, Synthesis and Properties Of (3–Quinuclidyl)Diarylcarbinols, Khim. Geterosikl Soedin, 7, 1976, 776–780.

Sekine et al, Effect of Sulfur Containing Purine Nucleosides on Immunological Reaction in Mice, Japan, J. Exp. Med, 1973, vol. 43, 5, pp. 369–375.

De Vito et al, Synthesis and Pharmacological Evaluation of Some Novel 13–[N,N][dialkylamino–alkyl]benzo[g][2]benzopyrano [4,3–b]indol–5[13H]ones, Med. Chem. Res., 1(1), (1991), pp, 47–51.

Ermakov et al, Application Of Mass Spectrometry in Structural And Stereochemical Investigations . . . , Khim. Geterosikl Soedin, 10, (1975), 1376–1383.

Mikhlina et al, Stereochemistry Of Benzo[b]Quinuclidines . . . , Khim. Geterosikl Soekin, 6, (1973), pp. 839–843.

Fleet et al., Complex Quinuclidines (1–Azabicyclo[2,2,2] octanes) from Sugars: Synthesis of 1α,3α,4α,5α)–Quinuclidine–3,5–diol from D–Glucose, J. Chem. Soc. Perkin, Trans, 1(5), (1989), 1067–1068.

QUINCLIDINE DERIVATIVES AS SQUALENE SYNTHASE INHIBITORS

This application is a 371 of PCT/GB93/01648, Aug. 4, 1993.

FIELD OF INVENTION

This invention concerns heterocyclic derivatives which are useful in inhibiting squalene synthase, processes for their preparation and pharmaceutical compositions containing them. The present invention is also concerned with methods of using such heterocyclic derivatives in diseases and medical conditions where inhibition of squalene synthase is desirable, for example in treating diseases or medical conditions such as hypercholesterolemia and atherosclerosis.

BACKGROUND TO INVENTION

Several different classes of compounds have been reported to possess the capability of being able to lover cholesterol levels in blood plasma. For example agents which inhibit the enzyme HMG CoA reductase, which is essential for the production of cholesterol, have been reported to reduce levels of serum cholesterol. Illustrative of this class of compounds is the HMGCoA reductase inhibitor known as lovastatin which is disclosed in U.S. Pat. No 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol, which results in an upregulation of the heptatic LDL receptor and thus in a lowering of circulating blood cholesterol levels.

Squalene synthase is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovascular disease. Thus, an agent which inhibits squalene synthase should be useful in treating diseases and medical conditions in which a reduction in the levels of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

Quinuclidine derivatives have been reported in, for example, EP 458,214, U.S. Pat. No. 4,599,344, U.S. Pat. No. 3,725,410, GB 1,416,958, Khim, Farm, 12(11), (1978), 56–60; Khim. Farm, 7(8), (1973), 20–24, Heterocycles, 24, (1986), 971–7 Khim. Geterotsikl. Soedin, 3, (1983), 381–5, and 7, (1976), 776–780.

Disclosure of Invention

The present invention is based on the discovery that certain heterocyclic derivatives are inhibitors of squalene synthase, and are hence useful in treating diseases and medical conditions in which inhibition of squalene synthase is desirable.

According to the present invention there is provided the use of a compound of formula I (formula set out hereinafter together with the other chemical formulae referred to herein), or a pharmaceutically-acceptable salt thereof, wherein:

$R^1$ is hydrogen or hydroxy;

$R^2$ is hydrogen;

or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, (1–4C)alkylenedioxy, (1–6C)alkanoyl and oxime derivatives thereof and O-(1–6C)alkyl ethers of said oximes; provided that when X is selected from —$OCH_2$—, —$NHCH_2$—, and —$S(O)_nCH_2$—, $R^1$ is not hydroxy;

for the manufacture of a medicament for treating diseases or medical conditions in which inhibition of squalene synthase is desirable.

The compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthase in a warm-blooded animal (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis. It will also be appreciated that certain compounds of formula I may exist as geometrical isomers. The invention includes any geometrical isomer of a compound of formula I which possesses the beneficial pharmacological effect of inhibiting squalene synthase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will be appreciated that when $R^1$ and $R^2$ are joined so that $CR^1$-$CR^2$ is a double bond, the heterocyclic ring in formula I will comprise the 2,3-dehydroquinuclidine moiety shown in formula Ia.

It will also be appreciated that oxime derivatives of an (1–6C)alkanoyl group will comprise aldoximes and ketoximes of the formula —C(Ra)=NOH in which Ra is hydrogen or (1–6C)alkyl, and O-ethers of these oximes will have the formula —C(Ra)=NORb in which Ra is hydrogen or (1–6C)alkyl and Rb is (1–6C)alkyl.

A particular value for an optional substituent which may be present on Ar, for example, for alkyl; (1–6C)alkyl, such as methyl, ethyl, propyl, isopropyl, butyl, isobutyl, sec-butyl, tert-butyl or pentyl;

for alkenyl; (2–4C)alkenyl, such as allyl, prop-1-enyl, 2-methyl-2-propenyl or 2-butenyl;

for alkynyl; (2–4C)alkynyl, such as prop-2-ynyl or but-2-ynyl;

for alkoxy; (1–6C)alkoxy, such as methoxy, ethoxy, propoxy, isopropoxy, butoxy, pentoxy or 3-methylbutoxy;

for alkylamino; (1–4C)alkylamino, such as methylamino, ethylamino, propylamino or butylamino;

for di-alkylamino; dimethylamino, diethylamino, methylpropylamino or dipropylamino;

for alkylcarbamoyl; N-methylcarbamoyl, N-ethylcarbamoyl, N-propylcarbamoyl, N-butylcarbamoyl, N-tert-butylcarbamoyl, N-pentylcarbamoyl (N-(2-methylpropyl)carbamoyl;

for di-alkylcarbamoyl; N,N-dimethylcarbamoyl or N,N-diethylcarbamoyl;

for alkoxycarbonyl; methoxycarbonyl, ethoxycarbonyl, propoxycarbonyl, iso-propoxycarbonyl, butoxycarbonyl or tert-butoxycarbonyl;

for alkylthio; methylthio, ethylthio, propylthio, isopropylthio or butylthio;

for alkylsulphinyl; methylsulphinyl, ethylsulphinyl, propylsulphinyl, isopropylsulphinyl or butylsulphinyl;

for alkylsulphonyl; methylsulphonyl, ethylsulphonyl, propylsulphonyl, isoproylsulphonyl or butylsulphonyl;

for halogeno; fluoro, chloro, bromo or iodo;

for halogenoalkyl; halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluoromethyl, difluoromethyl and fluoromethyl;

for alkanoylamino; formamido, acetamido, propionamido, iso-propionamido, butyramido or iso-butyramido;

for alkylenedixoy; methylenedioxy or ethylenedioxy;

for alkanoyl; formyl, acetyl, propionyl or butyryl; and for O-alkyl ethers; methyl, ethyl, propyl, isopropyl, and butyl of oximes ethers of oximes.

In general, it is preferred that, Ar may be unsubstituted phenyl or may be phenyl substituted by one, two or three substituents.

In particular, Ar is phenyl which optionally bears one or more substituents independently selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, halogeno(1–6C)alkyl, (1–6C)alkanoylamino, (1–6C)alkanoyl and oxime derivatives thereof and O-(1–6C)alkyl ethers of said oximes.

More particularly, Ar is phenyl which optionally bears one or more substituents independently selected from halogeno, amino, nitro, cyano, (1–6C)alkyl, (2–6C)alkenyl, (1–6C)alkoxy, (1–6C)alkylamino, di-[(1–6C)alkyl]amino, (1–6C)alkoxycarbonyl, halogeno(1–6C)alkyl, (1–6C)alkanoylamino, (1–6C)alkanoyl and a group of formula —C(Ra)=NORb in which Ra is (1–6C)alkyl and Rb is (1–6C)alkyl.

In general it is preferred, for example, that Ar is phenyl which is substituted by one or more substituents independently selected from halogeno, cyano, (1–6C)alkyl, (2–6C)alkenyl, (1–6C)alkoxy, (1–6C)alkoxycarbonyl, halogeno (1–6C)alkyl, (1–6C)alkanoylamino, (1–6C)alkanoyl and a group of formula —C(Ra)=NORb in which Ra is (1–6C) alkyl and Rb is (1–6C)alkyl.

Values of Ar of particular interest include, for example, phenyl which bears one or more substituents independently selected from halogeno, cyano, (1–6C)alkyl, (2–6C)alkenyl, (1–6C)alkoxy, (1–6C)alkoxycarbonyl, (1–6C)alkanoylamino, halogen (1–6C)alkyl, (1–6C)alkanoyl and a group of formula —C(Ra)=NORb in which Ra is (1–6C) alkyl and Rb is (1–6C)alkyl.

Values of Ar of special interest include 2-substituted-phenyl, 4-substituted-phenyl and 2,4-di-substituted-phenylphenyl, wherein the substituents are selected from those hereinbefore defined.

Specific values of Ar of particular interest include, for example, 4-butoxyphenyl, 2-allyl-4-ethoxycarbonylphenyl, 2-allyl-4-cyanophenyl, 4-tert-butoxycarbonylphenyl, 4-pentoxyphenyl, 4-acetylphenyl, 4-propoxyphenyl, 4-methylphenyl, 2,4-dichlorophenyl, 4-pentylphenyl, 2-allyl-4-ethoxycarbonylphenyl, 4-(3-methylbutyl)phenyl, 2-allyl-4-isopropoxycarbonylphenyl and 2-trifluoromethylphenyl.

Particular values for X include, for example, —CH$_2$CH$_2$—, —CH=CH—, —C≡C—, —CH$_2$O—, —CH$_2$NH— or —CH$_2$S—, more particularly —CH$_2$CH$_2$—, —CH=CH—, —C≡C— or —CH$_2$O—. It is generally preferred, for example, that X is —C≡C— or —CH$_2$O—, especially —C≡C—.

Particular values for $R^1$ and $R^2$ are when $R^1$ and $R^2$ are both hydrogen; or when $R^1$ is hydroxy and $R^2$ is hydrogen. It is preferred, for example, that $R^1$ is hydroxy and $R^2$ is hydrogen.

In one embodiment of the present invention $R^1$ and $R^2$ are both hydrogen; and X and Ar may take any of the values defined above. Particular, preferred and specific values include the appropriate values mentioned above.

In a second embodiment of the present invention $R^1$ is hydroxy; $R^2$ is hydrogen; and X and Ar may take any of the values defined above. Particular, preferred and specific values include the appropriate values mentioned above.

In a further embodiment of the present invention $R^1$ and $R^2$ are joined together so that $CR^1$–$CR^2$ is a double bond; and X and Ar may take any of the values defined above. Particular, preferred and specific values include the appropriate values mentioned above.

In a further embodiment of the present invention, $R^1$ is hydrogen or hydroxy; $R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S$— and —$SCH_2$—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino; provided that when X is selected from —$OCH_2$—, —$NHCH_2$—, and —$SCH_2$—, $R^1$ is not hydroxy.

Particular, preferred and specific values include the appropriate values mentioned above.

In a further embodiment of the present invention $R^1$ is hydrogen or hydroxy; $R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$CH_2NH$— and —$CH_2S$—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values include the appropriate values mentioned above.

In a further embodiment $R^1$ is hydrogen or hydroxy; $R^2$ is hydrogen; or $R^1$ and $R^2$ are joined together so that $CR^1$–$CR^2$ is a double bond; X is selected from —$CH_2CH_2$—, —CH=CH—, —C≡C—, —$CH_2O$—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values include the appropriate values mentioned above.

Many of the compounds of the present invention are novel and are provided as a further feature of the present invention.

Thus, according to the present invention there is also provided a compound of formula I, or a pharmaceutically-acceptable salt thereof, wherein:

$R^1$ is hydrogen or hydroxy;

$R^2$ is hydrogen;

or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— wherein n is 0,1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, (1–4C)alkylenedioxy, (1–6C)alkanoyl and oxime derivatives thereof and O-(1–6C)alkyl ethers of said oximes; provided that when X is selected from —$OCH_2$—, —$NHCH_2$—, and —$S(O)_nCH_2$—, $R^1$ is not hydroxy;

R1 is hydroxy, R2 is hydrogen, X is —$CH_2CH_2$— and Ar is 4-chlorophenyl;

R1 and R2 are hydrogen, X is —$OCH_2$— and Ar is phenyl or 3-chlorophenyl;

R1 and R2 are hydrogen, X is —$SCH_2$— and Ar is 4-methoxyphenyl;

R1 and R2 are hydrogen, X is —CH=CH— and Ar is phenyl, 3,4-dichlorophenyl, 3-chlorophenyl or 4-chlorophenyl;

R1 and R2 are hydrogen, X is —$CH_2CH_2$— and Ar 4-chlorophenyl;

R1 and R2 are hydrogen, X is —$CH_2NH$— and Ar is phenyl;

R1 and R2 are hydrogen, X is —$CH_2CO$— and Ar is phenyl, 4-trifluoromethylphenyl, 4-chlorophenyl, 4-methoxyphenyl, 4-fluorophenyl or 3-trifluoromethylphenyl;

R1 and R2 are hydrogen, X is —$NHCH_2$— and Ar is phenyl, 3,4-dimethoxyphenyl or 2-chlorophenyl; and R1 and R2 are hydrogen, X is —$CH_2O$— and Ar is phenyl.

Particular, preferred and specific values include the appropriate values mentioned above.

In one embodiment there is provided a compound of formula I, or a pharmaceutically-acceptable salt thereof, wherein:

$R^1$ is hydroxy; $R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-

[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, (1–4C)alkylenedioxy, (1–6C)alkanoyl and oxime derivatives thereof and O-(1–6C)alkyl ethers of said oximes; provided that when X is selected from —OCH$_2$—, —NHCH$_2$—, and —S(O)$_n$CH$_2$—, R$^1$ is not hydroxy; and excluding the compound in which R1 is hydroxy, R2 is hydrogen, X is —CH$_2$CH$_2$— and Ar is 4-chlorophenyl and its pharmaceutically acceptable salt.

Particular, preferred and specific values include the appropriate values mentioned above. Thus, for example, it is generally preferred that R$^1$ is hydroxy and R$^2$ is hydrogen.

In a further embodiment, there is provided a compound of formula I, or a pharmaceutically-acceptable salt thereof, wherein:

R$^1$ is hydrogen; R$^2$ is hydrogen;

X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —CH$_2$S(O)$_n$— and —S(O)$_n$CH$_2$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, (1–4C)alkylenedioxy, (1–6C)alkanoyl and oxime derivatives thereof and O-(1–6C)alkyl ethers of said oximes; but excluding those compounds in which X is —CH$_2$CH$_2$— and Ar is 4-chlorophenyl;

X is —OCH$_2$— and Ar is phenyl or 3-chlorophenyl;

X is —SCH$_2$— and Ar is 4-methoxyphenyl;

X is —CH=CH— and Ar is phenyl, 3,4-dichlorophenyl, 3-chlorophenyl or 4-chlorophenyl;

X is —CH$_2$CH$_2$— and Ar 4-chlorophenyl;

X is —CH$_2$NH— and Ar is phenyl;

X is —CH$_2$CO— and Ar is phenyl, 4-trifluoromethylphenyl, 4-chlorophenyl, 4-fluorophenyl, 4-methoxyphenyl or 3-trifluoromethylphenyl;

X is —NHCH$_2$— and Ar is phenyl, 3,4-dimethoxyphenyl or 2-chlorophenyl; and

X is —CH$_2$O— and Ar is phenyl; and their pharmaceutically acceptable salts.

Particular, preferred and specific values for R1, R2, X and Ar include those mentioned above.

In particular when R1 is hydroxy or hydrogen, R2 is hydrogen and X is —CH$_2$CH$_2$—, Ar is not halogenophenyl; more particularly Ar is not phenyl optionally substituted by a halogeno, hydroxy, alkyl, alkoxy, amino, cyano, nitro, alkanoylamino, carbamoyl, alkylsulphonyl or alkylcarbamoyl substituent.

In particular when R1 and R2 are hydrogen, X is not —CH$_2$O—, —OCH$_2$—, —CH$_2$S(O)$_n$— or —S(O)$_n$CH$_2$—;

when R1 and R2 are hydrogen and X is —CH$_2$CO—, Ar is not phenol optionally substituted by one more groups selected from trifluoromethyl, halogeno and (1–6C)alkoxy;

when R1 and R2 are hydrogen and X is —NHCH$_2$—, Ar is not phenyl optionally substituted by one or more groups selected from (1–6C)alkoxy and halogeno;

when R1 and R2 are hydrogen, X is —CH=CH—, then Ar is not phenyl optionally substituted by one or more halogeno groups; and when R1 and R2 are hydrogen and X is —CH$_2$NH—, Ar is not phenyl.

In a particular embodiment, R$^1$ is hydrogen or hydroxy; R$^2$ is hydrogen; or R$^1$ and R$^2$ are joined together so that CR$^1$–CR$^2$ is a double bond;

X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —CH$_2$S— and —SCH$_2$—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values include the appropriate values mentioned above.

In a group of compounds of formula I of particular interest R$^1$ is hydroxy; R$^2$ is hydrogen; or R$^1$ and R$^2$ are joined together so that CR$^1$–CR$^2$ is a double bond;

X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —CH$_2$S(O)$_n$— and —S(O)$_n$CH$_2$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, (1–4C)alkyleneoxy, (1–6C)alkanoyl and oxime derivatives thereof and O-(1–6C)alkyl ethers of said oximes; provided that when X is selected from —OCH$_2$—, —NHCH$_2$—, and —SCH$_2$—, R$^1$ is not hydroxy; and when R1 is hydroxy, R2 is hydrogen and X is —CH$_2$CH$_2$—, Ar is not phenyl optionally substituted by a halogeno, hydroxy, alkyl, alkoxy, amino, cyano, nitro, alkanoylamino, carbamoyl, alkylsulphonyl or alkylcarbamoyl substituent.

Particular, preferred and specific values include the appropriate values mentioned above.

In a preferred group of compounds, R$^1$ is hydroxy; R$^2$ is hydrogen; X is selected from —CH$_2$CH$_2$—, —CH=CH—, —C≡C—, —CH$_2$O—, —CH$_2$NH—, —CH$_2$CO—, —COCH$_2$— and —CH$_2$S—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)

alkylthio, (1–6C)alkylsulphinyl, (1–6C) alkylsulphonyl, halogeno (1–6C)alkyl and (1–6C) alkanoylamino; excluding the compound in which X is —$CH_2CH_2$— and Ar is 4-chlorophenyl.

Particular, preferred and specific values include the appropriate values mentioned above.

Thus in a further embodiment of the present invention there is provided a compound of formula I, or a pharmaceutically acceptable salt thereof, wherein $R^1$ is hydrogen or hydroxy; $R^2$ is hydrogen; or $R^1$ and $R^2$ are joined together so that $CR^1$–$CR^2$ is a double bond;

X is selected from —CH=CH—, —C≡C— or —$CH_2O$—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino; provided that when R1 and R2 are both hydrogen and X is —$CH_2O$—, then Ar is not unsubstituted phenyl; and when $R^1$ and $R^2$ are both hydrogen, then Ar is not phenyl.

Particular, preferred and specific values include the appropriate values mentioned above. In a particular embodiment, for example, when X is —$CH_2O$—, then $R^1$ is hydroxy and $R^2$ is hydrogen.

In a specific embodiment of the present invention $R^1$ is hydrogen or hydroxy; $R^2$ is hydrogen;

X is —C≡C—; and

Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values include the appropriate values mentioned above.

Compounds of the invention which are of particular interest include the compounds described in the accompanying Examples (and their pharmaceutically-acceptable salts), and are hence provided as a further feature of the present invention. Thus, in particular the present invention provides a compound selected from:

3-(4-ethoxycarbonyl-2-allylphenoxymethyl)-3-hydroxyquinuclidine;
3-(2-allyl-4-cyanophenoxymethyl)-3-hydroxyquinuclidine;
3-[2-(4-butoxyphenyl)vinyl]quinuclidine;
3-[2-(4-butoxyphenyl)ethynyl]-3-hydroxyquinuclidine;
3-[2-(4-pentoxyphenyl)ethynyl]-3-hydroxyquinuclidine;
3-[2-(4-pentylphenyl)ethynyl]-3-hydroxyquinuclidine;
3-[2-(4-ethoxycarbonyl-2-allylphenyl)ethynyl]-3-hydroxyquinuclidine; and
3-(2-allyl-4-isopropoxycarbonylphenoxymethyl)-3-hydroxyquinuclidine; and their pharmaceutically acceptable salts.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example, $R^1$, $R^2$, X and Ar may take any of the meanings hereinbefore defined.

Thus, according to the present invention there is also provided a process for preparing a compound of formula I, or a pharmaceutically-acceptable salt thereof, which process comprises:

(a) For those compounds of formula I in which $R^1$ and $R^2$ are both hydrogen, reducing a compound of formula I in which $R^1$ and $R^2$ are joined together so that $CR^1$–$CR^2$ is a double bond.

The reduction may be carried out, for example, by catalytic hydrogenation, or by reaction with a suitable reducing agent. Suitable reaction conditions include, for example, catalytic hydrogenation using a catalyst which comprises a noble metal. Particular catalysts include palladium, platinum and nickel (especially when in the finely divided state known as raney nickel), and catalysts in which the noble metal is supported on an inert carrier such as carbon. A specific example of a supported catalyst is Pd/C. The reduction is conveniently carried out in a solvent of, for example, an alcohol (such as ethanol), and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example, 0°–60° C. It may be preferable to cool the reaction below ambient temperature (e.g. to about 0° C.) during the reduction. The borane generated may be hydrolysed by treatment with an organic acid such as acetic acid, which hydrolysis may be carried out at 0°–60° C., and may be accelerated by heating (e.g. refluxing).

(b) For compounds of formula I in which $R^1$ and $R^2$ are joined together so that $CR^1$–$CR^2$ is a double bond, dehydrating a compound of formula I in which $R^1$ is hydroxy and $R^2$ is hydrogen.

The dehydration may be carried out using an acid such as sulphuric acid (e.g. concentrated sulphuric acid), or p-toluene sulphonic acid. The reaction is conveniently carried out with heating, and conveniently an inert solvent is employed. For example, the reaction may be carried out using sulphuric acid at temperatures of about 70°–130° C.; or using p-toluene sulphonic acid in a hydrocarbon solvent of, for example, toluene or xylene at ambient temperature to reflux, and preferably at reflux. The dehydration may also be carried out using trifluoroacetic acid in an inert solvent such as dichloromethane (at ambient temperature to reflux temperature).

For values of X such as $CH_2O$ and $CH_2S$ the process described in (c) below will, in general, be employed.

(c) For compounds of formula I in which $R^1$ and $R^2$ are joined together so that $CR^1$-$CR^2$ is a double bond, treating a compound of formula II in which Z is a leaving group with a base.

Suitable values for Z include, for example, halogen such as chloro, bromo, iodo, or a methylsulphonyloxy or toluenesulphonyloxy group. Suitable bases include hydroxide (such as potassium or sodium hydroxide), and alkoxide (such as potassium t-butoxide or sodium ethoxide).

The reaction is conveniently carried out in the presence of a solvent, preferably a polar organic solvent. Suitable solvents include, for example, an alcohol (such as ethanol), or an aprotic solvent such as dimethylformamide or N-methylpyrrolidone. The reaction may be carried out at ambient temperature or at an elevated temperature, such as at a temperature between ambient and the reflux temperature of the reaction mixture. This method is generally preferred over that described in (b) when X is $-OCH_2-$ or $-SCH_2-$.

The compounds of formula II may be prepared from a compound of formula I in which $R^1$ is hydroxy. For example, where Z is halogen the compound of formula I in which $R^1$ is hydroxy and $R^2$ is hydrogen may be reacted with the appropriate phosphorous halide (e.g. $PCl_5$, $PBr_3$ or $PI_3$), or where Z is chloro, by reaction with thionyl chloride. The compound of formula I in which $R^1$ is hydroxy may be reacted with mesyl chloride to the compound in which Z is methylsulphonyloxy; and with tosyl chloride to give Z is toluene sulphonyloxy.

(d) For those compounds of formula I in which X is $-CH_2CO-$, reacting an organometallic compound of formula III in which M is a metal atom or a derivative thereof, with a compound of formula IV.

Suitable values for M include, for example, magnesium and lithium. In the case where M is magnesium it is conveniently present in the form of a derivative of formula $-MgX$ where X is a halogen atom such as iodo or bromo, so that the organometallic compound of formula III is in the form known as a Grignard Reagent. The reaction is generally carried out in an inert solvent such as dry diethyl ether or tetrahydrofuran. For example, the reaction may be carried out at a temperature between 0° C. and the reflux temperature of the reaction mixture.

The compounds of formula III may be prepared from the corresponding compound of formula Ar-"hal" in which "hal" is a halogen atom, such as iodo or bromo as is well known in the art.

e) For those compounds of formula I in which X is $-CH_2-NH-$ or $-NHCH_2-$, reducing a compound of formula I in which X is $-CH=N-$ or $-N=CH-$ (as appropriate).

The reaction may be carried out using a chemical reducing agent such as a hydride in a solvent such as an alcohol at ambient temperature. Thus, in a particular example, the reduction may be carried out using sodium borohydride in a solvent of methanol at ambient temperature. The reduction may also be carried out by selective catalytic hydrogenation using similar conditions to those described under (a) above.

It will be appreciated that the preferred method of reduction will depend upon the value of X. Thus, for example, where debenzylation is possible (e.g. when X is $-NHCH_2-$), it is generally preferred that a chemical reducing agent is employed.

The compounds of formula I in which X is $-CH=N-$ may be prepared by reaction of a compound of formula V with a compound of formula VI. The reaction is generally carried out in an inert hydrocarbon solvent such as toluene or benzene, with heating (e.g. at reflux) and the reaction may be accelerated by removing water generated in the reaction by azeotropic distillation. Similarly, the compounds of formula I in which X is $-N=CH-$ may be prepared by reaction of a compound of formula VII with a compound of formula VIII.

f) For those compounds of formula I in which X is $-CH_2NH-$, $-CH_2O-$, $-CH_2S-$, $R^1$ is hydroxy and $R^2$ is hydrogen, reacting a compound of formula IX in which Z is $-NH_2$, $-OH$ or SH as appropriate with a compound of formula X.

The reaction is conveniently carried out in a solvent such an inert hydrocarbon e.g. toluene with heating. The reaction may be facilitated by the presence of acid or base.

The compound of formula X is preferably generated in situ, by, for example, treating quinuclidin-3-one with trimethylsulphoxonium iodide in the presence of a base of, for example, an alkali metal hydride such as sodium hydride and in a solvent such as dimethylformamide, or an alkali metal hydroxide such as sodium hydroxide in a solvent such as an aqueous solvent.

The compound of formula X may also be prepared from a "halohydrin" as is well known in the art. The halohydrin may be prepared, for example, by addition of HOCl to the corresponding olefin and the halohydrin treated with base (e.g. NaOH) to give the compound of formula X.

g) For compounds of formula I in which X is $-CH=CH-$, reacting a compound of formula XI with a compound of formula V in the presence of a base.

Suitable bases include alkoxides, such as potassium t-butoxide, and the reaction is conveniently carried out in an inert solvent such as tetrahydrofuran with cooling below ambient temperature e.g. $-40°$ C. to $0°$ C.); and metal hydrides such as sodium hydride in a solvent such as dimethyl formamide or dimethylsuphoxide. A particularly suitable base is, for example, sodium dimsyl which may conveniently be used in a solvent such as dimethyl suphoxide.

The compounds of formula XI may be prepared by reaction of a compound of formula $ArCH_2$-hal in which "hal" is halogen, such as chloro, with triphenylphosphine as is well known in the art.

h) For those compounds of formula I in which X is $-CH_2CH_2-$, reducing a compound of formula I in which X is $-CH=CH-$.

The reaction may conveniently be carried out by catalytic hydrogenation using conditions similar to those mentioned in (a) above.

In an alternative synthesis a compound of formula $ArCH_2CH_2$-hal wherein "hal" represents a halogen atom such as bromo, is reacted with quinuclidin-3-one in the presence of sec-butyl lithium, with cooling (e.g. $-70°$ C.) in an inert solvent such as tetrahydrofuran.

i) For compounds of formula I in which X is $-COCH_2-$, reacting a compound of formula XII in which M is a metal atom or a derivative thereof, with a compound of formula XIII.

Suitable values for H and suitable reaction conditions are those mentioned in (d) above. The compounds of formula XII may be prepared from the corresponding halogeno compound in a manner analogous to the preparation of compounds of formula III discussed in (d) above.

j) For those compounds of formula I in which X is —CH$_2$O— or —CH$_2$S—, reacting a compound of formula XIV with a compound of formula XV, in which $Z^1$ is a leaving group and $Z^2$ is —YM, or $Z^1$ is —YM and $Z^2$ is a leaving group, and wherein Y is oxygen or sulphur (as appropriate) and M is a metal atom.

Suitable leaving groups include, for example, halogen (such as chloro, bromo or iodo), methanesulphonyloxy, toluenesulphonyloxy or trifluoromethanesulphonyloxy; and suitable metals include, for example sodium and lithium.

The process is generally performed in the presence of a suitable solvent, for example, a hydrocarbon, such as toluene or xylene, or an ether such as dioxan or tetrahydrofuran, and at a temperature in the range, for example 20°–150° C.

It may be desirable to protect the quinuclidine nitrogen atom during the reaction, especially when $Z^1$ is —YM, as described in (1) below. It may be desirable to protect $R^1$ when it represents a hydroxy group as, for example, a silyl ether.

k) For those compounds of formula I in which X is —OCH$_2$— or —SCH$_2$— and $R^1$ and $R^2$ are both hydrogen, reacting a compound of formula XVI in which Y is oxygen or sulphur as appropriate with a compound of formula XVII in which Z is a leaving group.

Suitable leaving groups include halogen, such as chloro, bromo or iodo, methanesulphonyloxy and toluenesulphonyloxy. The reaction is generally carried out in the presence of a base such as an alkali metal hydroxide, e.g. sodium or potassium hydroxide, and in a solvent such as dimethylsulphoxide or dimethylformamide.

l) For compounds of formula X in which X is —OCH$_2$—, —SCH$_2$—, —CH$_2$O—, or —CH$_2$S—, deprotecting a compound of formula XVIII in which Q is a protecting group.

Suitable values for Q include, for example, —BH$_3$ or an oxygen atom. When Q is —BH$_3$ the deprotection may be carried out by treatment with an acid such as hydrochloric acid in a solvent such as acetone. When Q is an oxygen atom deprotection may be carried out by reduction using a suitable reducing agent such as sulphur dioxide.

The compounds of formula XVIII in which X is —CH$_2$O— or —CH$_2$S— may be prepared by methods analogous to those described in (j), and in which X is —OCH$_2$— or —SCH$_2$— by methods analogous to these described in (k) above, but in which the starting material containing the quinuclidine moiety is protected by Q. A preferred way of preparing compounds of formula XVIII in which X is —CH$_2$O— or —CH$_2$S— and $R^1$ is hydroxy and $R^2$ is hydrogen is by a procedure analogous to that described in (f) in which the compound of formula X protected by Q is reacted with a compound of formula IX in dimethylformamide, in the presence of potassium carbonate. The quinuclidine moiety in the various starting materials may be protected using methodology well known in the art. Thus, for example, those in which Q is BH$_3$ may be prepared by reaction of the appropriate quinuclidine moiety with BH$_3$.THF, generally with cooling (for example at −70° C.); whilst those in which Q is an oxygen atom may be prepared by oxidation of the appropriate quinuclidine moiety with, for example, 30% hydrogen peroxide.

m) For those compounds of formula I in which X is —C≡C—, reacting a compound of formula I in which X is —CH=CH— with a halogen, followed by treatment with a base.

A suitable halogen is bromine and the reaction is conveniently carried out in an inert solvent such as carbon tetrachloride. Suitable bases include, for example, potassium t-butoxide. This treatment is conveniently carried out in a solvent such as THF, with heating (e.g. at a temperature between ambient and about 70° C.).

n) For those compounds of formula I in which $R^1$ is hydroxy, $R^2$ is hydrogen and X is —C≡C—, reacting a compound of formula XIX in which M is a metal atom, with quinuclidin-3-one.

A suitable metal is lithium and suitable reaction conditions include those mentioned in (d) above.

o) For those compounds in which $R^1$ and $R^2$ are hydrogen and X is —C≡C—, reacting a compound of formula XIX in which M is a metal atom with a compound of formula XV in which Z is a leaving group.

Suitable values for Z include, for example, halogen (such as chloro, bromo or iodo), methanesulphonyloxy, toluenesulphonyloxy or trifluoromethanesulphonyloxy; suitable values for M include, for example, lithium; and suitable reaction conditions include those mentioned under (d) above.

p) For those compounds in which X is —C≡C— and $R^1$ is hydrogen or hydroxy and $R^2$ is hydrogen, reacting a compound of formula XX with a compound of formula IX in which Z is a leaving group in the presence of a catalyst.

Suitable catalysts include, for example, transition metal complexes such as palladium or nickel complexes. Particular catalysts are palladium (II) complexes, a specific example of which is Pd(PPh$_3$)Cl$_2$. Suitable values for Z include, for example, halogen (such as chloro, bromo or iodo), methanesulphonyloxy, toluenesulphonyloxy and trifluoromethanesulphonyloxy. The reaction is generally carried out in the presence of a base, for example, an amine such as triethylamine and in a solvent such as dimethylformamide with heating (for example at 60° to 100° C.). The reaction is preferably carried out in the presence of copper (I)iodide. Compounds of formula XX may be prepared according to Scheme 1a and 2b.

q) For those compounds in which X is —C≡C— and $R^1$ is hydrogen or hydroxy and $R^2$ is hydrogen, reacting a compound of formula XXI with a compound of formula IX in which Z is a leaving group in the presence of a catalyst.

Suitable reaction conditions are those mentioned under (p) above. Compounds of formula XXI may be prepared according to Scheme 1b and 2a.

r) For those compounds in which X is —CH=CH—, reducing a compound of formula I in which X is —C≡C—.

The reaction may be carried out by catalytic hydrogenation using conditions similar to those mentioned in (a) above. A particularly suitable catalyst is, for example, Lindlars catalyst (Pd on BaSO$_4$ poisoned with quinoline). The reaction may also be carried out using a reducing agent such as those mentioned under (a) above or lithium aluminium hydride in a suitable solvent such as diethylether at ambient temperature or with cooling.

s) For those compounds of formula I in which X is —CH=CH—, reacting a compound of formula XXII in which L is a suitable ligand with a compound of formula IX in which Z is a leaving group in the presence of a catalyst.

Suitable values for L include, for example, (1–6C)alkyl with butyl being preferred. Suitable values for Z, suitable catalysts and reaction conditions include those mentioned under (p) above. A particularly suitable catalyst is, for example, tris(dibenzylidine acetone)palladium [O].

The compounds of formula I in which X is —SCH$_2$— may be oxidised to these in which the sulphur atom bears an oxygen atom (that is to a "sulphoxide") using, for example an appropriate quantity of sodium periodate. Further oxidation to the compound in which the sulphur atom bears two oxygen atoms (that is a "sulphone") may be carried out using a peracid such as peracetic acid or hydrogen peroxide. The oxidation of sulphur compounds to the corresponding sulphoxides and sulphones is well known in the chemical art. Compounds of formula I in which X is —CH$_2$S— may be oxidised to the corresponding sulphoxides or sulphones in the same way.

In some cases oxidation of compounds of formula I to give a sulphone may be accompanied by some oxidation of the nitrogen atom in the quinuclidine ring to the N-oxide. In such cases the quinuclidine N-oxide moiety may be reduced back to a quinuclidine moiety without affecting the sulphone using reducing agents well known in the art, such as sulphur dioxide.

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthetase. Thus the compounds of the present invention inhibit cholesterol biosynthesis by inhibition of *de novo* squalene production.

The beneficial pharmacological properties of the compounds of the present invention may be demonstrated using one or more of the following techniques.

(a) Inhibition of Squalene Synthetase

In this test, the ability of a compound to prevent the formation of squalene from a radioactive substrate (tritiated farnesyl pyrophosphate) is assessed.

The test compound is incubated at a concentration of 25 micromolar in 200 µl of a buffered solution containing potassium phosphate (50 mM), MgCl$_2$ (4.95 mM), KF (9.9 mM), NADPH (0.9 mM) and rat liver microsomal protein (20 µg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 µM, and stopped after 15 minutes reaction time with the addition of 50 µl of 4% KOH. The reaction products are separated from unreacted substrate after application to a C-18 octadecyl 1 ccBond column (Analytichem Int product No. 617101). An aqueous fraction is eluted with 250 µl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The IC$_{50}$ (concentration which results in a 50% inhibition of squalene production), of the test compound can be determined by testing the compound at several, for example five, concentrations predicted from the two concentration results. The IC$_{50}$ can then be determined from a plot of percentage inhibition against concentration of test compound.

In general, compounds of formula I show significant inhibition in the above test at a concentration in the range of about 0.001 to 25 µM.

By way of illustration of the squalene synthetase inhibitory properties of the compound of formula I, the compound described in Example 4 below gave an IC$_{50}$ of $3.3 \times 10^{-8}$M.

(b) Acute rat cholesterol synthesis assay.

This is an acute in vivo test in the rat to measure de novo hepatic cholesterol synthesis from exogenously administered $^{14}$C-acetate.

Female rats (35–55 g) are housed in reverse lighting conditions (red light from 0200 h–1400 h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 µCi [2-$^{14}$C]-acetate (NEN DUPONT. specific activity, 45–60 mCi/mmol NEC-085H, or AMERSHAM specific activity, 50–60 mCi/mmol CFA 14) in a volume of 0.25 ml saline (100 µCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. $EC_{50}$ values can be determined in the standard way.

In general, compounds of formula I show activity in the range of about 0.1 to 100 mg/kg.

By way of illustration, the compound described in Example 18 gave an $ED_{50}$ of about 21.5 mg/kg.

No overt toxicity was detected when compounds of the formula I were administered at several multiples of their minimum inhibitory dose or concentration.

As mentioned previously, the compounds of the present invention are squalene synthetase inhibitors and hence possess the property of inhibiting cholesterol biosynthesis. Thus the compounds of the present invention will be useful in treating diseases or medical conditions in which a lowering of cholesterol is blood plasma is desirable, for example, hypercholesterolemia and/or ischaemic diseases associated with atheromatous vascular degeneration such as atherosclerosis.

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessarily the maximum attainable by diligent process development;

(v) proton NMR spectra were normally determined at 200 MHz in $DMSOd_6$ using tetramethylsilane (TMS) as a internal standard, and are expressed as chemical shifts (delta values) in parts per million relative to TMS using conventional abbreviations for designation of major peaks: s, singlet; m, multiplet; t, triplet; br, broad; d, doublet;

(vi) all end-products were characterised by microanalysis, NMR and/or mass spectroscopy; and (vii) conventional abbreviations are used for individual radicals and recrystallisation solvents, for example, Me=methyl, Et=ethyl, Pr=Propyl, Pr$^i$=isopropyl, Bu=butyl, Bu$^i$=isobutyl, Ph=phenyl; EtOAc=ethyl acetate, Et$_2$O=ether, MeCN=acetonitrile, MeOH= methanol, EtOH=ethanol, Pr$^i$OH=2-propanol, H$_2$O= water.

EXAMPLE 1

A solution of sodium hydroxide (8.8 g) in water (90 ml) was added to a stirred mixture of quinuclidin-3-one (9.2 g), 4-butoxyphenol (12.2 g) and trimethylsulphoxonium iodide (32.4 g) in toluene (150 ml). The mixture was stirred at room temperature for 64 hours under an atmosphere of argon. The mixture was extracted with ethyl acetate (4×100 ml). The ethyl acetate extracts were combined, washed with 2M sodium hydroxide solution (2×50 ml), water (2×50 ml) and then extracted with 2M hydrochloric acid (3×35 ml).

The acidic extracts were combined, cooled to 5° C. and then basified by the addition of 11M sodium hydroxide solution (25 ml). The aqueous mixture was extracted with ethyl acetate (4×70 ml) and the ethyl acetate extracts were combined, washed with saturated brine (50 ml), dried (Na$_2$SO$_4$) and evaporated. The residue was purified by flash column chromatography on silica gel (2 g, Merck 7736) to give 3-(4-butoxyphenoxymethyl)-3-hydroxyquinuclidine (1.5 g) as a colourless solid, m.p. 110°–112° C.; microanalysis, found: C, 70.7; H, 9.0; N, 4.7%; C$_{18}$H$_{27}$NO$_3$ requires: C,70.8; H, 8.9; N, 4.6%; NMR (CDCl$_3$): 1.0(3H, t), 1.2–1.8(7H, m), 2.1(2H, m), 1.8–2.6(1H, br), 2.6–3.1(6H, m), 3.9(2H, t), 4.0(1H, d), 3.8(1H, d) and 6.8(4H, br s); m/z 306 (M+H).

EXAMPLE 2

The procedure described in Example 1 was repeated using 2-allylphenol (9.6 g), instead of 4-butoxyphenol, to prepare 3-(2-allylphenoxymethyl)-3-hydroxyquinuclidine which was dissolved in acetone and a solution of hydrogen chloride in ether added to afford 3-(2-allylphenoxymethyl)-3-hydroxyquinuclidine hydrochloride as a colourless solid, m.p. 102°–128° C.; microanalysis, found: C, 64.7; H, 8.0; N, 4.5% C$_{17}$H$_{23}$NO$_2$.HCl.0.3H$_2$O requires C, 64.8; H, 7.9; N, 4.4%; NMR (DMSO-d6): 1.6–1.8(1H, m), 1.7–2.0(2H, m), 2.1–2.3(2H, m), 3.0–3.5(8H, m), 4.0–4.1(2H, q), 5.0–5.1 (2H, m), 5.5(1H, s), 5.9–6.1(1H, m), 6.8–7.0(2H, m), 7.1–7.3(2H, m) and 10.7(1H, br); m/z 274 (M+H).

EXAMPLE 3

Potassium-tert-butoxide (2.46 g) was added to a stirred, ice-cooled suspension of (4-butoxybenzyl)-triphenylphosphonium bromide (10.1 g) in dry tetrahydrofuran (300 ml) under an atmosphere of argon. The reaction mixture was stirred at room temperature for 1 hour. The reaction mixture was cooled to −10° C. and a solution of 3-formylquinuclidine (750 mg) in dry tetrahydrofuran (20 ml) was added dropwise over 15 minutes. The reaction mixture was stirred at room temperature overnight and water (1.0 ml) was then added. The tetrahydrofuran was evaporated and the residue was triturated several times with ether and filtered. The ether extracts were combined and evaporated to give an oil which was purified by flash column chromatography, using 10% methanol in dichloromethane containing 1% 0.880 ammonia as eluent, to give Z-3-[2-(4-butoxyphenyl)vinyl]-quinuclidine (Rf=0.3). This was dissolved in ether and an excess of a solution of hydrogen chloride in ether added to give a solid which was collected by filtration. There was thus obtained Z-3-[2-(4-butoxyphenyl)vinyl]quinuclidine hydrogen chloride as a colourless solid, m.p. 146°–149° C. (220 mg); microanalysis, found: C, 68.2; H, 8.4; N, 4.2%; C$_{19}$H$_{27}$NO.HCl.0.75H$_2$O requires: C, 68.06; H, 8.8; N, 4.18%; NMR (DMSO-d$_6$): 0.9–0.97(3H, t), 1.35–1.49(2H, m), 1.66–2.16(8H, m), 2.82–2.95(1H, m), 3.08–3.3(4H, m), 3.41–3.58(1H, t), 3.9–4.03(2H, t), 5.65–5.78(1H, d of d), 6.43–6.53(1H, d, J=11 Hertz), 6.9–7.0(2H, d) and 7.16–7.26 (2H, d); m/Z 286 (M+H).

Further elution with the above eluent gave a mixture of E-Z-3-[2-(4-butoxyphenyl)vinyl]quinuclidine (600 mg), followed by pure E-3-[2-(4-butoxyphenyl)vinyl]quinuclidine (Rf=0.19) which was converted to its hydrochloride salt using a solution of hydrogen chloride in ether as described above to give E-3-[2-(4-butoxyphenyl)vinyl]-quinuclidine hydrochloride (120 mg), m.p. 235°–238° C.; microanalysis, found: C, 69.0; H, 8.5; N, 4.1% C$_{19}$H$_{27}$NO.HCl.0.5H$_2$O requires: C, 68.98; H, 8.77; N, 4.25%; NMR (DMSO-d$_6$): 0.89–0.97(3H, t), 1.3–1.52(2H, m), 1.62–1.8(3H, m), 1.82–2.1(5H, m), 2.75–2.92(1H, m), 2.98–3.52(5H, m), 3.91–4.01(2H, 6.2–6.34(1H, d of d), 6.41–6.55(1H, d, J=15.98 Hertz), 6.82–6.93(2H, d) and 7.31–7.41 (2H, d); m/Z 286 (M+H).

EXAMPLE 4

A mixture of E/Z isomers of 3-[2-(4-butoxyphenyl)vinyl)] quinuclidine hydrogen chloride (600 mg), palladium-on-charcoal (5% w/w, 100 mg) and ethanol (50 ml) was stirred under an atmosphere of hydrogen until no further hydrogen uptake occured. The mixture was filtered and the filtrate was evaporated to give a colourless solid residue which was crystallised from acetone to give 3-[2-(4-butoxyphenyl) ethyl]-quinuclidine hydrochloride (200 mg), m.p. 189°–190° C.; microanalysis, found: C, 70.3; H, 9.4; N, 4.2%; C$_{19}$H$_{29}$NO.HCl requires: C, 70.5; H, 9.27; N, 4.32%; NMR (DMSO-d$_6$): 0.88–1.0(3H, t); 1.35–1.42(2H, m), 1.6–2.0(10H, m), 2.7–2.85(1H, m), 3.02–3.22(4H, m), 3.3–3.47(1H, m), 3.89–3.98(2H, t), 6.78–6.88(2H, d), 7.1–7.2(2H, d) and 10.0–1.02(1H, br); m/Z 288 (M+H).

EXAMPLE 5

A mixture of 3-ethynyl-3-hydroxyquinuclidine (750 mg), 4-butoxyiodobenzene (1.38 g), bis(triphenylphosphine)-palladium (II) chloride (175 mg), copper (I) iodide (88 mg), triethylamine (5.0 ml) and dimethylformamide (10 ml) was stirred at 75° C. under an atmosphere of argon for 2 hours. The triethylamine and dimethylformamide were removed by evaporation. A solution of sodium hydroxide (2M, 10 ml) was added to the residue and the mixture extracted with dichloromethane (3×20 ml). The organic extracts were combined, dried (MgSO$_4$) and evaporated to give a solid residue. This residue was dissolved in ethyl acetate, treated with activated carbon, filtered and the filtrate treated with excess of a solution of hydrogen chloride in ether to give 3-[2-(4-butoxyphenyl)ethynyl]-3-hydroxyquinuclidine hydrochloride as a solid (1.17 g), m.p. 177°–179°; microanalysis, found: C, 66.8; H, 7.5; N, 3.9%; C$_{19}$H$_{26}$NO$_2$.HCl.0.25H$_2$O requires: C, 67.05; H, 7.79; N, 4.11%; NMR (DMSO-d$_6$): 0.85–1.01(3H, t), 1.32–1.55(2H, m), 1.6–1.85(2H, m), 1.85–2.3(5H, m), 3.0–3.6(6H, m), 3.9–4.1(2H, t), 6–3–6.5(1H, br), 6.86–7.0(2H, d), 7.3–7.44 (2H, d) and 10.38–10.52(1H, br); m/Z 300 (M+H).

The 3-ethynyl-3-hydroxyquinuclidine used as starting material was obtained as follows:

A solution of n-butyl lithium (100 ml of a 2M solution in pentane) was added portion-wise over a period of 20 minutes to a stirred solution of ethynyltrimethylsilane (19.6 g) in dry tetrahydrofuran (400 ml) at −70° C. The mixture was stirred for 1 hour at −70° C. A solution of 3-quinuclidone (24 g) in dry tetrahydrofuran (100 ml) was then added to the mixture and the mixture stirred for 1 hour at −70° C. Methanol (1 ml) was then added to the mixture and the mixture allowed to warm to room temperature. The solvents were removed by evaporation. Methanol (500 ml) and potassium carbonate (40 g) were added to the residue and the mixture was stirred for 1 hour. The solvent was removed by evaporation. The residue was triturated with water (500 ml) and then dried in vacuo to give 3-ethynyl-3-hydroxyquinuclidine as a solid (21.2g), m.p. 193°–197° C.; NMR (DMSO-d$_6$): 1.25–1.3(1H, m), 1.4–1.6(1H, m), 1.7–1.95 (3H, m), 2.55–2.8(5H, m), 2.95(1H, d), 3.2(1H, s) and 5.4(1H, s); m/Z 152 (M+H).

EXAMPLE 6

A mixture of 3-ethynyl-3-hydroxyquinuclidine (302 mg), 4-iodoacetanilide (522 mg), bis(triphenylphosphine)-palladium (II) chloride (70 mg), copper (I) iodide (35 mg), triethylamine (2 ml) and DMF (4 ml) was heated at 65° C. under an atmosphere of argon for 4 hours. The reaction mixture was cooled then poured into 5% sodium carbonate solution (10 ml) and the resulting mixture extracted with ethyl acetate (3×5 ml). The organic extracts were combined, dried (MgSO$_4$) and evaporated to give a solid residue. This residue was purified by flash column chromatography using a mixture of 10% methanol in dichloromethane containing 1% 0.880 ammonia as eluent to give 3-[2-(4-acetamidophenyl)ethynyl]-3-hydroxyquinuclidine (180 mg), m.p. 198° to 205° C. (with decomposition); microanalysis, found: C, 67.9; H, 7.0; N, 9.5%; C$_{17}$H$_{20}$N$_2$O$_2$.H$_2$O requires: C, 67.55; H, 7.28; N, 9.27%; NMR (DMSO-d$_6$): 1.3–1.45(1H, m), 1.56–1.7(1H, m), 1.8–2.0(3H, m), 2.06(3H, s), 2.7–2.8(4H, t), 2.85–2.92(1H, d), 3.1–3.17(1H, d), 5.65(1H, s), 7.3–7.35(2H, d), 7.55–7.6 (2H, d) and 10.1(1H, br); m/Z 285 (M+H).

EXAMPLE 7

A mixture of 3-ethenyl-3-hydroxyquinuclidine (306 mg), 4-butoxyphenyliodobenzene (552 mg), bis-(triphenylphosphine)-palladium (II) chloride (70 mg), copper (I) iodide (35 mg), triethylamine (10 ml) and dimethylformamide (10 ml) was stirred at 90° C. under an atmosphere of argon for 6 hours. The mixture was evaporated and the residue purified by flash column chromatography using a gradient of 5% methanol in dichloromethane containing 0.5% 0.880 ammonia to 15% methanol in dichloromethane containing 1% 0.880 ammonia as eluent. There was thus obtained E-3-[2-(4-butoxyphenyl)ethenyl]-3-hydroxyquinuclidine hydroiodide as a solid (after trituration with ethyl acetate), m.p. 166°–169° C.; microanalysis, found: C, 52.4; H, 6.5; N, 3.2; I, 29.0%; C$_{19}$H$_{27}$NO$_2$.HI.0.25H$_2$O requires: C, 52.6; H, 6.57; N, 3.22; I, 29.3%; NMR (DMSO-d$_6$): 0.9–1.0(3H, t), 1.3–1.55(2H, m), 1.62–1.8(2H, m), 1.8–1.95(3H, m), 1.95–2.0(1H, s), 2.1–2.32(1H, br), 3.0–3.5(6H, m), 3.9–4.0(2H, t), 5.55(1H, s), 6.38–6.46(1H, d, J=16.5 Hertz), 6.65–6.73(1H, d, J=16.5 Hertz), 6.86–6.98(2H, d), 7.32–7.44(2H, d) and 9.4–9.6(1H, br); m/Z 302 (M+H).

The 3-ethenyl-3-hydroxyquinuclidine used as starting material was prepared as follows:

A mixture of 3-ethynyl-3-hydroxyquinuclidine (5.0 g), palladium on calcium carbonate (5 % w/w, 0.5 g) and ethanol (200 ml) was stirred under an atmosphere of hydrogen until 900 ml of hydrogen has been consumed. The mixture was filtered and evaporated to give 3-ethenyl-3-hydroxyquinuclidine (5.0 g) as an oil which gave a solid on standing and was used without further purification, m.p. 76°–80° C.; NMR(DMSO-d$_6$): 1.2(1H, m), 1.4–1.6(3H, m), 2.0(1H, m), 2.45–2.85(6H, m), 4.55(1H, s), 5.0(1H, d of d), 5.25(1H, d of d), 6.1(1H, d of d); m/z 154 (M+H).

The 3-ethynyl-3-hydroxyquinuclidine was prepared as described in Example 5.

EXAMPLE 8

A mixture of 3-ethynyl-3-hydroxyquinuclidine (604 mg), ethyl 4-iodobenzoate (1.1 g), bis(triphenylphosphine)-palladium (II) chloride (140 mg), copper (I) iodide (70 mg) and anhydrous triethylamine (4 ml) and anhydrous dimethylformamide (8 ml) was stirred under an atmosphere of argon. The reaction mixture was heated at 65° C. for 18 hours. The reaction mixture was cooled and the triethylamine and dimethylformamide removed by evaporation. To the residue was added 2M sodium hydroxide (25 ml) and the mixture extracted with dichloromethane. The organic phase was washed with water, saturated brine and dried (MgSO$_4$). Evaporation gave a solid which was crystallised from acetonitrile to give 3-[2-(4-ethoxycarbonylphenyl)ethynyl]-3-hydroxyquinuclidine (553 mg) as a colourless solid, m.p. 176°–177° C.; microanalysis, found: C, 72.2; H, 7.3; N, 4.8%; C$_{18}$H$_{21}$NO$_3$ requires: C, 72.2; H, 7.07; N, 4.68%; NMR (DMSO-d$_6$): 1.32(3H, t), 1.49–2.01(5H, m), 2.68(4H, t), 2.78–3.14(2H, d of d), 4.32(2H, q), 5.66(1H, br.s), 7.49–7.58(2H, d) and 7.90–7.98(2H, d); m/Z 300 (M+H).

EXAMPLE 9

An aqueous solution of 3M hydrochloric acid (7 ml) was added to a solution of 3-(4-acetamido-2-allylphenoxymethyl)-3-hydroxyquinuclidine borane complex (1.2 g) in acetone (21 ml) at 5° C. under an atmosphere of argon. The solution was stirred for 1 hour at 5° C. and then evaporated to low bulk. The residue was diluted with 2M hydrochloric acid (30 ml) and washed with ethyl acetate (2×50 ml). The acidic aqueous layer was basified with solid sodium carbonate and extracted with ethyl acetate (3×70 ml). The ethyl acetate extracts were combined, dried (Na$_2$SO$_4$) and evaporated. The residue was crystallised from acetone (10 ml) to give 3-(4-acetamido-2-allylphenoxymethyl)-3-hydroxyquinuclidine (0.5 g) as a colourless solid, m.p. 170°–172° C.; microanalysis, found: C, 69.0; H, 8.1; N, 8.7%; C$_{19}$H$_{26}$N$_2$O$_3$ requires: C, 69.1; H, 7.9; N, 8.5%; NMR (DMSO-d$_6$): 1.1–1.3(1H, m), 1.4–1.7 (2H, m), 1.8–2.2(5H, m), 2.5–2.9(6H, m), 3.7–4.0(2H, q), 4.6(1H, s), 4.9–5.6(2H, m), 5.8–6.1(1H, m), 6.8–7.0(1H, d), 7.3(1H, d), 7.3–7.5(1H, d of d) and 9.7(1H, s); m/z 331 (M+H).

The 3-(4-acetamido-2-allylphenoxymethyl)-3-hydroxyquinuclidine borane complex used as starting material was obtained as follows:

A solution of borane-tetrahydrofuran complex (135 ml of a 1M solution in tetrahydrofuran) was added portionwise over a period of 30 minutes to a stirred solution of 3-quinuclidinone (16.9 g) in dry tetrahydrofuran (300 ml) at –70° C. The mixture was stirred at –70° C. for 30 minutes. Water (20 ml) was added to the reaction mixture at –70° C. The solvent was removed by evaporation. A saturated solution of brine (250 ml) was added to the residue and the mixture basified by addition of solid sodium carbonate. The mixture was extracted with dichloromethane (4×100 ml). The dichloromethane extracts were combined, silica gel (Merck 9385, 60 g) added and the mixture evaporated to give a free flowing powder. This pre-absorbed material on silica gel was purified by flash column chromatography on a further portion of silica gel using a mixture of 25% ethyl acetate/pentane as eluent to give 3-quinuclidinone borane complex (17.0 g) as a colourless solid, m.p. 162°–164° C.; NMR (CDCl$_3$): 0.7–2.3(3H, br), 2.0–2.3(4H, m), 2.7(1H, m), 3.0–3.4(4H, m) and 3.5(2H, s).

Powdered trimethyl sulphoxonium iodide (24.4 g) was added portionwise to a stirred, ice-cooled, suspension of sodium hydride (60% w/w dispersion in mineral oil, 4.4 g; the oil was removed by washing the solid with petroleum ether) in dry dimethyl formamide (140 ml) under an atmosphere of argon whilst maintaining the temperature at 10° to 15° C. The mixture was allowed to warm to room temperature. Solid 3-quinuclidinone borane complex (15.5 g) was added to the stirred mixture whilst maintaining the temperature at 25°–30° C. using an ice-bath. The mixture was then stirred at room temperature for 16 hours. The mixture was poured into water (1400 ml) and the mixture was extracted with ethyl acetate (4×400 ml).

The ethyl acetate extracts were combined, washed with water (3×300 ml), dried (Na$_2$SO$_4$) and evaporated. The residue was purified by flash column chromatography on silica gel using dichloromethane as eluent to give 3-methylenequinuclidine oxide borane complex (13.8 g) as a colourless solid, m.p. 74°–77° C.; microanalysis, found: C, 63.1; H, 10.6; N, 9.2%; $C_8H_{16}BNO$ requires: C, 62.8; H, 10.5; N, 9.2%; NMR ($CDCl_3$): 0.6–2.3(3H, br), 1.6(1H, m), 1.7–1.9(1H, m), 1.9–2.0(2H, m), 2.1–2.3(1H, m), 2.8(2H, q) and 2.9–3.4(6H, m); m/z 152 (M–H).

A mixture of 4-acetamido-2-allylphenol (1.4 g), 3-methylenequinuclidine oxide borane complex (1.1 g) and powdered potassium carbonate (2.1 g) in dry dimethyl formamide (10 ml) was heated at 70° C. under an atmosphere of argon for 3.5 hours. The mixture was poured into water (100 ml) and extracted with ethyl acetate (3×70 ml). The ethyl acetate extracts were combined, washed with 2M sodium hydroxide (2×40 ml), water (2×60 ml), dried ($Na_2SO_4$) and evaporated. The residue was purified by flash column chromatography on silica gel using a gradient of dichloromethane to 40% ethyl acetate/dichloromethane as eluent to give 3-(4-acetamido-2-allylphenoxymethyl)-3-hydroxyquinuclidine borane complex (2.6 g), as a colourless solid, m.p. 140°–143° C.; NMR ($CDCl_3$): 0.6–2.4(3H, br), 1.5–1.7(1H, m), 1.7–1.9(2H, m), 2.1(3H, s), 2.1–2.4(2H, m), 2.8(1H, s), 2.8–3.3(6H, m), 3.3–3.4(2H, d), 3.8–4.0(2H, q), 4.9–5.1(2H, m), 5.8–6.0(1H, m), 6.7–6.8(1H, d), 7.1–7.3 (2H, m) and 7.3–7.5(1H, m); m/z 343 (M–H).

EXAMPLE 10

The procedure described in Example 9 was repeated using 4-acetamidophenol (0.9 g), instead of 4-acetamido-2-allylphenol. There was thus obtained 3-(4-acetamidophenoxymethyl)-3-hydroxyquinuclidine (0.3 g) as a colourless solid, m.p. 185°–188° C.; microanalysis, found: C, 66.0; H, 7.9; N, 9.3%; $C_{16}H_{22}N_2O_3$ requires C, 66.2; H, 7.7; N, 9.7%; NMR (DMSO-$d_6$): 1.1–1.3(1H, m), 1.3–1.6(2H, m), 1.8–2.1(2H, m), 1.9(3H, s), 2.4–2.9(6H, m), 3.7–3.9(2H, q), 4.6(1H, s), 6.8–6.9(2H, d), 7.4–7.5(2H, d) and 9.7(1H, s); m/z 291 (M+H).

EXAMPLES 11–52

Using a procedure similar to that described in Example 5, the following compounds of formula 1, wherein X is —C≡C—, and $Y^2$ and $Y^4$ have the indicated values, were prepared from the corresponding compounds of formula 2 in which Z is iodo unless stated otherwise with purification and exceptions as noted. Where the compound of formula 2 is not commercially available preparative details are given.

EXAMPLE 11

$Y^2=H$, $Y^4=NO_2$

Purified on alumina (ICN N 32–63) using a 5% ethanol in ethyl acetate as eluent to give the title compound as a solid, m.p. 237°–240° C.; NMR: 1.2–1.4(1H,m), 1.5–1.7(1H,m), 1.8–2.02(3H,m), 2.6–2.8(4H,m), 2.82–2.92(1H,d), 3.05–3.15(1H,d), 5.72(1H,s), 7.62–7.71(2H,d) and 8.18–8.27(2H,d).

EXAMPLE 12

$Y^2=H$, $Y^4=CH_3$

Purified by flash column chromatography on silica gel using a gradient of 10% methanol in dichloromethane containing 1% ammonia (density, 0.88 g/cm³) to 20% methanol in dichloromethane containing 1% ammonia (density, 0.88 g/cm²) as eluent to give the title compound as a solid, m.p. 179°–182° C.; NMR: 1.2–1.4(1H,m), 1.5–1.7(1H,m), 1.8–2.02(3H,m), 2.32(3H,s), 2.6–2.8(4H,m), 2.82–2.92(1H, d), 3.05–3.15(1H,d), 5.5(1H,s), 7.12–7.22(2H,d) and 7.25–7.35(2H,d).

EXAMPLE 13

$Y^2=H$, $Y^4=OCH_3$

Purified by preparative HPLC (Gilson Dynamax—60A column) using 80% methanol in water containing 0.5% triethylamine as eluent to give the title compound as a solid, m.p. 172°–173° C.; NMR: 1.2–1.4(1H,m), 1.5–1.7(1H,m), 1.8–2.02(3H,m), 2.6–2.8(4H,m), 2.82–2.92(1H,d), 3.05–3.15(1H,d), 3.8(3H,s), 5.55(1H,s), 6.9–6.97(2H,d) and 7.3–7.37(2H,d).

EXAMPLE 14

$Y^2=H$, $Y^4=OH$

Purified by preparative HPLC (Gilson Dynamax—60A column) using a mixture of 80% methanol in water containing 0.5% triethylamine as eluent to give the title compound, NMR: 1.2–1.4 (1H,m), 1.5–1.7(1H,m), 1.8–2.02(3H,m), 2.6–2.8(4H,m), 2.82–2.92(1H,d), 3.05–3.15(1H,d), 5.55 (1H,s), 6.7–6.79(2H,d), 7.17–7.26(2H,d) and 9.5–10.1(1H, br).

The compound of formula 2 was prepared as follows.

A solution of t-butyl-dimethylsilyl chloride (3.0 g) in dichloromethane (10 ml) was added dropwise to a stirred solution of 4-iodophenol (4.4 g) and imidazole (1.4 g) in dichloromethane (90 ml) whilst maintaining the temperature between 10° C. and 5° C. After the addition was complete, the reaction mixture was stirred for a further 4 hours at ambient temperature. The reaction mixture was washed with water, dried ($MgSO_4$), and evaporated to give 4-(t-butyldimethylsilyloxy)iodobenzene as a colourless oil (6.4 g) NMR(DMSO-$d_6$): 0.0(6H,s), 0.8(9H,s), 6.49–6.58(2H,d), 7.35–7.44(2H,d); m/z=334 (M).

EXAMPLE 15

$Y^2=H$, $Y^4=COCH_3$

Purified by flash column chromatograph on silica gel using 10% methanol in dichloromethane containing 1% ammonia (density, 0.88 g/cm³) as eluent to give the title compound as a solid m.p. 192°–193° C.: NMR: 1.2–1.4(1H, m), 1.5–1.7(1H,m), 1.8–2.02(3H,m), 2.6(3H,s), 2.6–2.8(4H, m), 2.82–2.92(1H,d), 3.05–3.15(1H,d), 5.7(1H,s), 7.55(2H, d) and 7.95(2H,d).

EXAMPLE 16

$Y^2=H$, $Y^4=NHCOCH_2CH_2CH_3$

Purified by crystallisation from acetonitrile to give the title compound as a solid, m.p. 179°–182° C.; NMR (run at 100° C.): 0.9–1.0(3H,t), 1.4–1.55(1H,m), 1.6–1.8(3H,m), 1.9–2.13(3H,m), 2.3–2.38(2H,t), 2.8–2.95(4H,m), 2.96–3.08(1H,d), 3.18–3.3(1H,d), 5.35(1H,br), 7.3–7.35 (2H,d), 7.56–7.61(2H,d) and 9.65(1H,s).

The compound of formula 2 used as starting material was prepared as follows.

4-iodoaniline (6.57 g) was added portionwise to butyric anhydride (30 ml) with stirring at ambient temperature. The reaction mixture was stirred at 100° C. for 20 minutes. The reaction mixture was allowed to cool to ambient temperature and n-hexane (50 ml) was added.

The solid precipiated during the reaction was collected by filtration, washed with n-hexane and dried to give 4-iodobutyranilide (6.8 g), m.p. 138°–139° C.; microanalysis, found: C, 41.6; H, 4.2; N, 4.5%; $C_{10}H_{12}INO$ requires: C, 41.5; H, 4.18; N, 4.84%; NMR: 0.85–0.95(3H, t), 1.5–1.7(2H,m), 2.2–2.32(2H,t), 7.39–7.48(2H,d), 7.57–7.66(2H,d), 9.91(1H,s); m/z 290(M+H).

EXAMPLE 17

$Y^2=Cl$, $Y^4=Cl$

Purified by crystallisation from acetonitrile to give the title compound as a solid, m.p. 153°–156° C.; NMR (run at 100° C.): 1.2–1.4(1H,m), 1.5–1.7(1H,m), 1.8–2.02(3H,m), 2.6–2.8(4H,m), 2.82–2.92(1H,d), 3.05–3.15(1H,d), 5.8(1H, br), 7.4–7.44(1H,d of d), 7.52–7.58(1H,d), and 7.62–7.65 (1H,d).

EXAMPLE 18

$Y^2=H$, $Y^4=n$-pentyl

Purified by crystallisation from acetone to give the title compound as a solid, m.p. 153°–155° C.; NMR: 0.8–0.91 (3H,t), 1.2–1.42(5H,m), 1.5–1.68(3H,m), 1.8–2.0(3H,m), 2.52–2.62(2H,t), 2.6–2.77(4H,m), 2.77–2.87(1H,d), 3.0–3.1 (1H,d), 5.56(1H,s), 7.12–7.22(2H,d) and 7.25–7.35(2H,d).

EXAMPLE 19

$Y^2=Pr^i$, $Y^4=COCH_3$

Purified by crystallisation from acetonitrile to give the title compound as a solid, m.p. 140°–142° C.; NMR: 1.2–1.4 (1H,m), 1.5–1.7(1H,m), 1.8–2.02(3H,m), 2.25(3H,s), 2.6–2.8(4H,m), 2.82–2.92(1H,d), 3.05–3.15(1H,d), 3.55 (2H,d), 5.0(2H,m), 5.65(1H,s), 6.0(1H,m), 7.5(1H,d) and 7.8(2H,m).

The compound of formula 2 used as starting material was prepared as follows from 3-allyl-4-hydroxyacetophenone using the method described in Example 29; NMR: 2.6(3H, s), 3.5–3.52(2H,d), 5.05–5.18(2H,m), 5.85–6.01(1H,m), 7.53–7.57(1H,m) and 7.92–8.07(2H,m).

EXAMPLE 20

$Y^2=OCH_3$, $Y^4=CO_2Et$

Purified by flash column chromatography on silica gel using 10% methanol in dichloromethane containing 1% ammonia (density, 0.88 g/cm³) as eluent to give the title compound as a solid, m.p. 141°–142° C.; NMR: 1.2–1.4 (1H,m), 1.33(3H,t), 1.5–1.7(1H,m), 1.8–2.02(3H,m), 2.6–2.8(4H,m), 2.82–2.92(1H,d), 3.05–3.15(1H,d), 3.88 (3H,s), 4.33(2H,q), 5.58(1H,s) and 7.43–7.56(3H,m).

The compound of formula 2 (Z=triflate) used as starting material was prepared as follows.

4-ethoxycarbonyl-2-methoxyphenyltriflate was prepared from ethyl vanillate using the procedure described in Example 29 for the preparation of 2-allyl-4-ethoxycarbonyl phenyltriflate. The product was an oil; NMR(CDCl₃): 1.40 (3H,t), 3.97(3H,s), 4.40(2H,q), 7.28(1H,d), 7.65–7.74(2H, m), m/z 329(M+H).

EXAMPLE 21

$Y^2=OEt$, $Y^4=CHO$

Purified by flash column chromatography on silica gel using a of 10% methanol in dichloromethane containing 1% ammonia (density, 0.88 g/cm³) as eluent to give the title compound as a solid, m.p. 148°–153° C.; NMR: 1.2–1.4 (1H,m), 1.45(3H,t), 1.5–1.7(1H,m), 1.8–2.02(3H,m), 2.6–2.8(4H,m), 2.65–3.15(1H,m), 2.82–2.92(1H,d), 3.05–3, 15(1H,d), 4.13(2H,q), 7.35(2H,d), 7.50(1H,d) and 9.93(1H, s).

The compound of formula 2 (Z=triflate) was prepared as follows.

4-carboxaldehyde-2-ethoxyphenyl triflate was prepared from ethyl vanillin using the procedure described in Example 29 for the preparation of 2-allyl-4-ethoxycarbonylphenyltriflate. The product was an oil; NMR (CDCl₃): 1.50(3H,t), 4.22(2H,q), 7.36–7.58(3H,m), 9.97 (1H,s); m/z 299(M+H).

EXAMPLE 22

$Y^2=H$, $Y^4=CO_2C(CH_3)_3$

Purified by crystallisation from acetonitrile to give the title compound as a solid, m.p. 186°–187° C.; NMR: 1.2–1.4 (1H,m), 1.5–1.7(1H,m), 1.63(9H,s), 1.8–2.02(3H,m), 2.6–2.8(4H,m), 2.82–2.92(1H,d), 3.05–3.15(1H,d), 5.79 (1H,s), 7.60(2H,d) and 7.96(2H,d).

The compound of formula 2 used as starting material was prepared as follows.

To a mixture of 4-iodobenzoic acid (2.58 g) in toluene (15 ml) at 80° C. under an atmosphere of argon was added, over 35 minutes, N,N-dimethylformamide di-tert-butyl acetal (10 ml). The reaction mixture was heated for a further 1 hour, cooled to ambient temperature, washed with water, saturated sodium bicarbonate, saturated brine, dried (MgSO₄) and evaporated to give an oil (2.3 g); NMR: 1.53(9H,s), 7.85–7.94(2H,d), 7.61–7.68(2H,d); m/z 305(M+H).

EXAMPLE 23

$Y^2=H$, $Y^4=CO_2CH(CH_3)_2$

Purified by crystallisation from acetonitrile to give the title compound as a solid, m.p. 188°–189° C.; NMR: 1.2–1.4 (1H,m), 1.31(6H,d), 1.5–1.7(1H,m), 1.8–2.02(3H,m), 2.6–2.8(4H,m), 2.82–2.92(1H,d), 3.05–3.15(1H,d), 5.14(1H quintet), 5.68(1H,s), 7.54(2H,d) and 7.92(2H,d).

The compound of formula 2 used as starting material was prepared as follows.

Thionyl chloride (1.4 ml) was added to a solution of 4-iodobenzoic acid (3.72 g) in isopropanol (25 ml) and the reaction mixture heated at 50° C. for several hours. The reaction mixture was cooled to ambient temperature and evaporated. Methylene chloride was added to the residue and the mixture filtered. The filtrate was washed with saturated sodium bicarbonate solution, water, saturated brine, dried (MgSO₄) and evaporated to give isopropyl-4-iodo-benzoate as an oil (1.5 g); NMR: 1.28–137(6H,d), 5.04–5.21(1H,m), 7.65–7.74(2H,d), 7.88–7.95(2H,d); m/z 291(M+H).

EXAMPLE 24

$Y^2=H$, $Y^4=OCH_2CH_2CH_3$

Purified by flash column chromatography on silica gel using 10% methanol in dichloromethane containing 1% ammonia (density, 0.88 g/cm³) as eluent to give the title compound as a solid, m.p. 163°–164° C.; NMR: 0.97(3H,t), 1.2–1.4(1H,m), 1.5–1.7(1H,m), 1.72(2H,m), 1.8–2.02(3H, m), 2.6–2.8(4H,m), 2.82–2.92(1H,d), 3.05–3.15(1H,d), 3.94 (2H,t), 5.5(1H,s), 6.90(2H,d) and 7.33(2H,d).

The compound of formula 2 used as starting material was prepared as follows.

A mixture of 4-iodophenol (6.6 g), 1-iodopropane (5.1 g), anhydrous potassium carbonate (13.8 g) and acetone (100 ml) was stirred at reflux for 6 hours. Two further portions of 1-iodopropane were added after one hour (5.1 g) and two hours (5.1 g). The acetone was removed by evaporation, the residue was treated with water (100 ml) and the mixture extracted with dichloromethane (2×30 ml). The organic extracts were combined, dried (MgSO$_4$) and evaporated. The residue, an oil, was distilled at 150° C. and 0.5 mm pressure (using a Kugelrohr oven) to give 4-n-propoxyiodobenzene as a colourless oil (7.2 g), NMR (CDCl$_3$): 0.9–1.08(3H,t), 1.7–1.9(2H,m), 3.82–3.92(2H,t), 6.62–6.72(2H,d), 7.5–7.6(2H,d); m/z 262 (M).

EXAMPLE 25

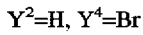
$Y^2$=H, $Y^4$=Br

Purified by flash column chromatography on silica gel using 10% methanol in dichloromethane containing 1% ammonia (density 0.88 g/cm$^3$) to give the title compound as a solid, m.p. 206°–208° C.; NMR: 1.2–1.4(1H,m), 1.5–1.7 (1H,m), 1.8–2.02(3H,m), 2.6–2.8(4H,m), 2.82–2.92(1H,d), 3.05–3.15(1H,d), 5.62(1H,s), 7.35(2H,d) and 7.56(2H,d).

EXAMPLE 26

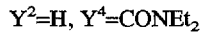
$Y^2$=H, $Y^4$=CONEt$_2$

Purified by flash column chromatography on silica gel using 10% methanol in dichloromethane containing 1% ammonia (density, 0.88 g/cm$^3$) as eluent, followed by re-crystallisation from acetonitrile, to give the title compound as a solid, m.p. 211°–212° C.; NMR: 1.08(6H,br), 1.2–1.4(1H,m), 1.5–1.7(1H,m), 1.8–2.02(3H,m), 2.6–2.8 (4H,m), 2.82–2.92(1H,d), 2.92–3.64(4H,br), 3.05–3.15(1H, d), 5.60(1H,s), 7.32(2H,d) and 7.45(2H,d).

The compound of formula 2 used as starting material was prepared as follows.

A mixture of 4-iodobenzoic acid (5 g) and thionyl chloride (30 ml) was heated at 70°–80° C. for 2 hours. The reaction mixture was cooled, the thionyl chloride evaporated and the resulting oil was azeotroped with toluene to give 4-iodobenzoyl chloride (5.38 g) as a solid which was used without further purification.

Diethylamine (1.14 ml) was added dropwise to a cooled solution of 4-iodobenzoyl chloride (2.66 g) and triethylamine (1.5 ml) in dry diethyl ether (30 ml) whilst under an atmosphere of argon. The reaction mixture was stirred at ambient temperature for 2 hours, the precipitated solid was removed by filtration and washed with diethyl ether. The filtrate was washed with water, saturated brine, dried (MgSO$_4$) and evaporated. The residue was purified by flash column chromatography on silica gel using 5% ethanol in ethyl acetate as eluent. There was thus obtained 4-iodo-N,N'-diethyl benzamide (2.67 g) as an oil; microanalysis, found: C, 43.9; H, 4.8; N, 4.4%; C$_{11}$H$_{14}$INO requires: C, 43.6; H, 4.66; N, 4.62%; NMR: 0.95–1.24(6H,br.s), 3.00–3.60(4H,br,m), 7.10–7.18(2H,d) and 7.75–7.84(2H,d); m/z 304 (M+H).

EXAMPLE 27

$Y^2$=H, $Y^4$=CONHC(CH$_3$)$_2$

Purified by flash column chromatography on silica gel using 10% methanol in dichloromethane containing 1% ammonia (density, 0.88 g/cm$^3$) as eluent to give the title compound as a solid, m.p.>250° C.; NMR: 1.2–1.4(1H,m), 1.36(9H,s), 1.5–1.7(1H,m), 1.8–2.02(1H,m), 2.6–2.8(4H, m), 2.82–2.92(1H,d), 3.05–3.15(1H,d), 5.65(1H,s), 7.44 (2H,d), 7.77(1H,s) and 7.80(2H,d).

The compound of formula 2 used as starting material was prepared in a similar manner to the starting material in Example 26 but using tert-butylamine in place of diethylamine. The product was purified by recrystallisation from 3% ethanol/ethyl acetate to give 4-iodo-N-t-butylbenzamide as a solid, m.p. 149°–150° C.; microanalysis, found: C, 43.9; H, 4.8; N, 4.4%; C$_{11}$H$_{14}$INO requires: C, 43.6; H, 4.66; N, 4.62%; NMR: 1.36(9H,s), 7.54–7.63(2H,d), 7.74–7.84(3H,m); m/z 304(M+H).

EXAMPLE 28

$Y^2$=H; $Y^4$=NEt$_2$

Purified by flash column chromatography on silica gel using 10% methanol in dichloromethane containing 1% ammonia (density, 0.88 g/cm$^3$) as eluent to give the title compound, NMR: 1.07(6H,t), 1.2–1.4(1H,m), 1.5–1.7(1H, m), 1.8–2.02(3H,m), 2.6–2.8(4H,m), 2.82–2.92(1H,d), 3.05–3.15(1H,d), 3.20–3.50(4H,q), 5.45(1H,s), 6.60(2H,d) and 7.16(2H,d).

The compound of formula 2 used as starting material was prepared as follows.

Sodium borohydride (5 g) was added portion-wise to a solution of 4-iodoaniline (4.38 g) in acetic acid (100 ml) at 15° to 20° C. under an atmosphere of argon. The temperature rose gradually during the addition to 50° C. The excess acetic acid was removed by evaporation. Water was added to the residue and the aqueous mixture was extracted with ethyl acetate. The organic phase was separated, washed with water, saturated brine, dried (MgSO$_4$) and evaporated. The residue was purified by flash chromatography on silica gel using 7% ethanol in ethyl acetate containing 1% triethylamine as eluent to give 4-iodo-N,N'-diethylaniline as an oil; microanalysis, found: C, 42.6; H, 4.7; N, 5.2%; C$_{10}$H$_{14}$IN requires: C,43.7; H, 5.13; N, 5.09%; NMR: 1.00–1.19(6H,t), 3.22–3.40(4H,q), 6.35–6.55(2H,m), and 7.28–7.43(2H,m); m/z 276(M+H).

EXAMPLE 29

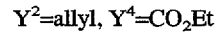
$Y^2$=allyl, $Y^4$=CO$_2$Et

Purified by flash column chromatography on silica gel using 10% methanol in dichloromethane containing 1% ammonia (density, 0.88 g/cm$^3$) as eluent, followed by recrystallisation from acetonitrile to give the title compound as a solid, m.p. 104°–105° C.; NMR: 1.2–1.4(1H,m), 1.31 (3H,t), 1.5–1.7(1H,m), 1.8–2.02(3H,m), 2.6–2.8(4H,m), 2.82–2.92(1H,d), 3.05–3.15(1H,d), 3.58(2H,d), 4.31(2H,q), 5.02–5.15(2H,m), 5.67(1H,s), 5.86–6.08(1H,m), 7.52(1H,d) and 7.76(2H,m).

The compound of formula 2 (Z=triflate) used as starting material was prepared as follows.

Triflic anhydride (2.8 ml) was added dropwise to an ice-cooled solution of ethyl-3-allyl-4-hydroxybenzoate (3.09 g) in pyridine (20 ml). The reaction mixture was stirred for 2 hours at 0° C. and then allowed to warm to +15° C. before pouring into water. The mixture was extracted with ethyl acetate. The organic layer was separated, washed with water, saturated brine, dried (MgSO$_4$) and evaporated. The residue was purified by flash column chromatography on silica gel using 1:1 (v/v) ethyl acetate/hexane as eluent to give 2-allyl-4-ethoxycarbonyl phenyl triflate as an oil (4.65 g), NMR (CDCl$_3$): 1.41(3H,t), 3.53(2H,d), 4.40(2H,q), 5.08–5.24(2H,m), 5.85–6.02(1H,m), 7.32–7.38(1H,d) and 7.95–8.05(2H,m); m/z 338(M$^+$).

EXAMPLE 30

Y$^2$=allyl, Y$^4$=NO$_2$

Purified by flash column chromatography on silica gel using 10% methanol in dichloromethane containing 1% ammonia (density, 0.88 g/cm$^3$) as eluent to give the title compound as a solid, m.p. 137°–138° C.; NMR: 1.2–1.4 (1H,m), 1.5–1.7(1H,m), 1.8–2.02(3H,m), 2.6–2.8(4H,m), 2.82–2.92(1H,d), 3.05–3.15(1H,d), 3.63(2H,d), 5.05–5.19 (2H,m), 5.74(1H,s), 5.91–6.09(1H,m), 7.65(1H,d) and 8.02–8.16(2H,m).

The compound of formula 2 (Z=triflate) used as starting material was prepared as follows.

Allyl 4-nitrophenyl ether was prepared using the procedure described in Example 55 for the preparation of allyl 4-cyanophenyl ether, but using 4-nitrophenol in place of 4-cyanophenol.

A mixture of allyl 4-nitrophenyl ether (78 g) and diphenyl ether (150 ml) was heated at 250° C. for 30 minutes. The reaction mixture was cooled to ambient temperature, and partitioned between diethyl ether and 2M aqueous sodium hydroxide solution. The aqueous layer was separated and acidified to pH3 with concentrated hydrochloric acid. The aqueous mixture was extracted with ethyl acetate the ethyl acetate extract dried (MgSO$_4$) and evaporated. The residue was purified by column chromatography on silica gel (Merck 7736) using a gradient of 0% to 20% methanol in dichloromethane as eluent to give 2-allyl-4-nitrophenol (21.4 g); microanalysis, found: C, 60.6; H, 5.1; N, 7.9%; C$_9$H$_9$NO$_3$ requires: C, 60.3; H, 5.06; N, NMR): 3.36(2H,d), 5.1(2H,m), 5.98(1H,m), 6.97(1H,d), 8.0(2H,m); m/z 197 (M+NH$_4$).

Triflic anhydride (1.63 ml) was added dropwise to a mixture of 2-allyl-4-nitrophenol (1.79 g) and 2,6-dimethylpyridine (1.18 g) in dry dichloromethane (15 ml) at −20° C. under an atmosphere of argon. The reaction mixture was allowed to reach ambient temperature over 3 hours. The mixture was partitioned between water and dichloromethane. The organic phase was separated, washed with 1M aqueous sodium hydroxide solution, water, dried (MgSO$_4$) and evaporated to give 2-allyl-4-nitrophenyl triflate (2.71 g) as an oil; microanalysis, found: C, 38.7; H, 2.6; N, 4.2%; C$_{10}$H$_8$F$_3$NO$_5$S requires: C, 38.6; H, 2.59; N, 4.5%; NMR: 3.7(2H,d), 5.19–5.35(2H,m), 5.97–6.17(1H,m), 7.84 (1H,d), 8.36–8.55(2H,m); m/z 311(M).

EXAMPLE 31

Y$^2$=n-Pr, Y$^4$=CO$_2$Et

Purified by flash column chromatography on silica gel using 10% methanol in dichloromethane containing 1% ammonia (density, 0.88 g/cm$^3$) as eluent to give the title compound as a solid, m.p. 135°–136° C.; NMR: 0.92(3H,t), 1.2–1.4(1H,m), 1.32(3H,t), 1.5–1.72(3H,m), 1.75–2.02(5H, m), 2.6–2.8(4H,m), 2.82–2.92(1H,d), 3.05–3.15(1H,d), 4.31 (2H,q), 5.68(1H,s), 7.45–7.52(1H,d) and 7.73–7.84(2H,m).

The compound of formula 2 (Z=triflate) used as starting material was prepared as follows.

A mixture of ethyl-3-allyl-4-hydroxybenzoate (4.12 g), palladium on carbon (10% w/w) and ethanol (100 ml) was stirred under an atmosphere of hydrogen until 500 ml of hydrogen had been consumed. The mixture was filtered and the filtrate was evaporated. The residue was purified by flash chromatography on silica gel using 4:1 (v/v) n-pentane/ethyl acetate as eluent to give ethyl-3-propyl-4-hydroxybenzoate (4.8 g) as a solid, m.p. 78°–79° C.; microanalysis, found: C, 69.2; H, 8.1%; C$_{12}$H$_{16}$O$_3$ requires: C, 69.2; H, 7.74%; NMR (CDCl$_3$): 0.97(3H,t), 1.38(3H,t), 1.67(2H,m), 2.60(2H,t), 4.35(2H,q), 5.71(1H,s), 6.79(1H,d) and 7.75–7.87(2H,m); m/z 209(M+H).

This was then converted to the triflate using the method described in Example 30.

EXAMPLE 32

Y$^2$=Me, Y$^4$ CO$_2$Et

Purified by flash column chromatography on silica gel using 10% methanol in dichloromethane containing 1% ammonia (density, 0.88 g/cm$^3$) as eluent to give the title compound as a solid, m.p. 150°–151° C.; NMR: 1.2–1.4 (1H,m), 1.34(3H,t), 1.5–1.7(1H,m), 1.8–2.02(3H,m), 2.45 (3H,s), 2.6–2.8(4H,m) 2.82–2.92(1H,d), 3.05–3.15(1H,d), 4.32(2H,q), 5.69(1H,s), 7.50(1H,d), 7.77(1H,d of d) and 7.86(1H,s).

The compound of formula 2 used as starting material was prepared by esterifying 4-bromo-3-methylbenzoic acid using ethanol and an acid catalyst of concentrated sulphuric acid.

EXAMPLE 33

Y$^2$=NO$_2$, Y$^4$=H

Purified by column chromatography on silica gel (Varian Bond Elut S1 silica gel) using a mixture of dichloromethane containing increasing amounts of methanol as eluent to give the title compound as a solid, m.p. 185.5° C.; NMR: 1.2–1.4(1H,m), 1.5–1.7(1H,m), 1.8–2.02(3H,m), 2.6–2.8 (4H,m), 2.82–2.92(1H,d), 3.05–3.15(1H,d), 7.49–7.8(3H,m) and 8.08(1H,d).

EXAMPLE 34

Y$^2$=CO$_2$Et, Y$^4$=H

Purified by column chromatography on silica gel (Varian Bond Elut S1 silica gel) using a mixture of dichloromethane containing increasing amounts of methanol as eluent to give the title compound as a solid, m.p. 128.9° C.; NMR: 1.2–1.4(1H,m), 1.32(3H,t), 1.5–1.7(1H,m), 1.8–2.02(3H, m), 2.6–2.8(4H,m), 2.82–2.92(1H,d), 3.05–3.15(1H,d), 4.3 (2H,q), 7.43–7.6(3H,m) and 7.81(1H,m).

EXAMPLE 35

Y$^2$=CF$_3$, Y$^4$=H

Purified by column chromatography on silica gel (Varion Bond Elut S1 silica gel) using a mixture of dichloromethane containing increasing amounts of methanol as eluent to give the title compound as a solid, m.p. 162.4° C.; NMR: 1.2–1.4(1H,m), 1.5–1.7(1H,m), 1.8–2.02(3H,m), 2.6–2.8 (4H,m), 2.82–2.92(1H,d), 3.05–3.15(1H,d) and 7.5–7.8(4H, m).

EXAMPLE 36

Y$^2$=CO$_2$Me, Y$^4$=H

Purified by column chromatography on silica gel (Varian Bond Elut S1 silica gel) using a mixture of dichloromethane containing increasing amounts of methanol as eluent to give the title compound as a solid, m.p. 165°–166° C.; NMR: 1.2–1.4(1H,m), 1.5–1.7(1H,m), 1.8–2.02(3H,m), 2.6–2.8 (4H,m), 2.82–2.92(1H,d), 3.05–3.15(1H,d), 3.83(3H,s), 7.4–7.65(3H,m) and 7.84(1H,d).

EXAMPLE 37

$Y^2$=H, $Y^4$=I

Purified by flash column chromatography on silica gel using a gradient of 5% methanol in dichloroethane containing 1% ammonia (density, 0.88 g/cm$^3$) to 15% methanol in dichloromethane containing 1% ammonia (density, 0.88 g/cm$^3$) as eluent, followed by re-crystallisation from ethanol to give the title compound as a solid, m.p. >290° C.; NMR: 1.2–1.4(1H,m), 1.5–1.7(1H,m), 1.8–2.02(3H,m), 2.6–2.8 (4H,m), 2.82–2.92(1H,d), 3.05–3.15(1H,d), 5.52(1H,s), 7.14–7.22(2H,d) and 7.69–7.77(2H,d).

EXAMPLE 38

$Y^2$=H, $Y^4$=CF$_3$

Purified by flash column chromatography on silica gel using 10% methanol in dichloromethane containing 1% ammonia (density, 0.88 g/cm$^3$) as eluent to give the title compound as a solid, m.p. 202°–203° C.; NMR: 1.2–1.4 (1H,m), 1.5–1.7(1H,m), 1.8–2.02(3H,m), 2.6–2.8(4H,m), 2.82–2.92(1H,d), 3.05–3.15(1H,d), 5.25(1H,s), 7.6(2H,d), and 7.75(2H,d).

EXAMPLE 39

$Y^2$=H, $Y^4$=CN

Purified by flash column chromatography on silica gel using methanol in dichloromethane containing 1% ammonia (density, 0.88 g/cm$^3$) as eluent to give the title compound as a solid, m.p. 241°–243° C.; NMR: 1.2–1.4(1H,m), 1.5–1.7 (1H,m), 1.8–2.02(3H,m), 2.6–2.8(4H,m), 2.82–2.92(1H,d), 3.05–3.15(1H,d), 5.7(1H,s), 7.6(2H,d) and 7.85(2H,d).

EXAMPLE 40

$Y^2$=H, $Y^4$=OCH$_2$CH$_2$CH(CH$_3$)$_2$

Purified by flash column chromatography on silica gel using 10% methanol in dichloromethane containing 1% ammonia (density, 0.88 g/cm$^3$) as eluent, followed by re-crystallisation from acetonitrile to give the title compound as a solid, m.p. 171°–172° C.; NMR: 0.84(6H,d), 1.2–1.4(1H,m), 1.4–1.6(3H,m), 1.5–1.7(1H,m), 1.6–1.9(1H,m), 1.8–2,02(3H,m), 2.6–2.8(4H,m), 2.82–2.92(1H,d), 3.05–3.15(1H,d), 3.91(2H,t), 5.41(1H,s), 6.83(2H,d) and 7.23(2H,d).

The compound of formula 2 used as starting material was prepared as follows.

Using the method described in Example 48 for the preparation of 4-cyanophenol allyl ether, 4-iodophenol was reacted with isoamylbromide in the presence of potassium carbonate to give 4-iodo-isoamyloxyphenol as an oil, NMR (CDCl$_3$): 0.95(6H,d), 1.66(2H,q), 1.68–1.92(1H,m), 3.93 (2H,t), 6.63–6.72(2H,d), 7.49–7.59(2H,d); m/z290(M).

EXAMPLE 41

$Y^2$=allyl, $Y^4$=CN

Purified by flash column chromatography on silica gel using 10% methanol in dichloromethane containing 1% ammonia (density, 0.88 g/cm$^3$) as eluent to give the title compound as a foam, NMR: 1.2–1.4(1H,m), 1.5–1.7(1H,m), 1.8–2.02(3H,m), 2.6–2.8(4H,m), 2.82–2.92(1H,d), 3.05–3.15(1H,d), 3.55(2H,d), 5.0–5.2(2H,m), 5.7(1H,s), 5.9–6.1(1H,m), 7.59(1H,d) and 7.65–7.8(2H,m).

The compound of formula 2 used as starting material was prepared using the method described in Example 55.

EXAMPLE 42

$Y^2$=CO$_2$Me, $Y^4$=NO$_2$

Purified by column chromatography on silica gel (Varian Bond Elut S1 silica gel) using dichloromethane containing increasing amounts of methanol as eluent to give the title compound as a solid, m.p. 300° C. (with decomposition); NMR: 1.2–1.4(1H,m), 1.5–1.7(1H,m), 1.8–2.02(3H,m), 2.6–2.8(4H,m), 2.82–2.92(1H,d), 3.05–3.15(1H,d), 3.95 (3H,s), 5.73(1H,s), 7.8(1H,d), 8.39(1H,m) and 8.59(1H,d).

EXAMPLE 43

$Y^2$=Et, $Y^4$=H

Purified by column chromatography on silica gel (Varian Bond Elut S1 silica gel) using dichloromethane containing increasing amounts of methanol as eluent to give the title compound as a solid, m.p. 121.9° C.; NMR: 1.19(3H,t), 1.2–1.4(1H,m), 1.5–1.7(1H,m), 1.8–2.02(3H,m), 2.6–2.8 (4H,m), 2.74(2H,q), 2.8–2.92(1H,d), 3.05–3.15(1H,d), 5.56 (1H,s) and 7.1–7.4(4H,m).

EXAMPLE 44

$Y^2$=O(CH$_2$)$_2$CH$_3$, $Y^4$=H

Purified by column chromatography on silica gel (Varian Bond Elut S1 silica gel) using dichloromethane containing increasing amounts of methanol as eluent to give the title compound as a solid, m.p. 132.1° C.; NMR: 1.0(3H,t), 1.2–1.4(1H,m), 1.5–1.7(1H,m), 1.75(2H,m), 1.8–2.02(3H,m), 2.6–2.8(4H,m), 2.82–2.92(1H,d), 3.05–3.15(1H,d), 3.96 (2H,t), 5.52(1H,s), 6.9(1H,t), 7.0(1H,d) and 7.3(2H,m).

EXAMPLE 45

$Y^2$=H, $Y^4$=—C(CH$_3$)=NOCH$_3$

Purified by flash column chromatography on silica gel using 10% methanol in dichloromethane containing 1% ammonia (density, 0.88 g/cm$^3$) as eluent to give the title compound as a solid, m.p. 210°–214° C.; NMR: 1.2–1.4 (1H,m), 1.5–1.7(1H,m), 1.8–2.02(3H,m), 2.2(3H,s), 2.6–2.8 (4H,m), 2.82–2.92(1H,d), 3.05–3.15(1H,d), 3.9(3H,s), 5.6 (1H,s), 7.4(2H,d) and 7.65(2H,d).

The compound of formula 2 used as starting material was prepared as follows.

A mixture of p-iodoacetophenone (0.98 g), O-methylhydroxylamine hydrochloride (0.34 g), sodium acetate (0.28 g), ethanol (8 ml) and water (2 ml) was heated at reflux for 1 hour. The reaction mixture was cooled to ambient temperature, diluted with aqueous sodium carbonate solution (100 ml) and the mixture extracted with ethyl acetate (100 ml). The ethyl acetate layer was separated, washed with brine, dried (K$_2$CO$_3$) and evaporated to give a solid which was used without further purification, NMR: 2.01(3H,s), 3.9(3H,s), 7.45(2H,m) and 7.8(2H,m).

EXAMPLE 46

$Y^2$=H $Y^4$=CONHCH$_2$CH(CH$_3$)$_2$

Purified by crystallisation from ethanol to give title compound as a solid, m.p. 238°–240° C.; NMR: 0.9(6H,d), 1.2–1.4(1H,m), 1.3(2H,m), 1.5–1.7(1H,m), 1.8–2.02(3H, m), 1.9(1H,m), 2.6–2.8(4H,m), 2.82–2.92(1H,d), 3.05–3.15 (1H,d), 5.6(1H,s), 7.45(2H,d), 7.85(2H,d) and 8.45(1H,m).

The compound of formula 2 used as starting material was prepared using the method described for the preparation of the compound of formula 2 in Example ??. There was thus obtained a solid, m.p. 144°–145° C.; NMR: 0.87(6H,d), 1.85(1H,m), 3.05(2H,m), 7.6(2H,m), 7.85(2H,m) and 8.48 (1H,m).

EXAMPLE 47

$Y^2$=H, $Y^4$=CONH(CH$_2$)$_4$CH$_3$

Purification by crystallisation from ethanol to give the title compound as a solid, m.p. 232°–234° C.; NMR: 0.88 (3H,d), 1.3(4H,m), 1.2–1.4(1H,m), 1.5(2H,m), 1.5–1.7(1H, m), 1.8–2.02(3H,m), 1.9(1H,m), 2.6–2.8(4H,m), 2.82–2.92 (1H,d), 3.05–3.15(1H,d), 3.25(2H,m), 5.6(1H,s), 7.45(2H, d), 7.85(2H,d) and 8.5(1H,t).

The compound of formula 2 used as starting material was prepared as follows.

A solution of 4-iodobenzoyl chloride (4.3 g) in dichloromethane (30 ml) was cooled to 5° C. and triethylamine (2.7 ml) was added, with stirring, followed by n-pentylamine (2.2 ml). The reaction mixture was stirred at 5° C. for 2 hours. Water was added to the mixture (30 ml). The organic phase was separated, washed with water, dried (MgSO$_4$) and evaporated to give a solid. The solid was collected by filtration and triturated with n-pentane to give a solid, (5.1 g), m.p. 146°–148° NMR: 0.85(3H,t), 1.25(4H, m), 1.5(2H,m), 3.22(2H,m), 7.65(2H,m), 7.82(2H,m), 8.45 (1H,m); m/z 318(M+H).

EXAMPLE 48

$Y^2$=Et, $Y^4$=CO$_2$CH$_3$

Purified by trituration using 10% diethylether in n-pentane to give a foam; NMR: 1.2(3H,t), 1.35(1H,m), 1.6(1H,m), 1.9(2H,m), 2.7(4H,m), 2.8(1H,d), 2.9(1H,d), 3.01(1H,d), 3.85(3H,t), 5.7(1H,s), 7.5(1H,d), 7.75(1H,m) and 7.85(1H,m).

The compound of formula 2 (Z=triflate) was prepared as follows.

A solution of 1-(3-ethyl-4-hydroxyphenol)ethanone—J. Pharm. Pharmacol., 8, (1958), 648–650 (10 g) in chloroform (50 cm$^3$) was added to a stirred solution of copper (II) bromide (22.7 g) in ethyl acetate (50 cm$^3$) at reflux. The reaction mixture was stirred at reflux for 1 hour. A further quantity of copper (II) bromide (4.7 g) was added to the reaction mixture and the reaction mixture heated at reflux for a further 4 hours. The reaction mixture, a suspension, was cooled to ambient temperature and filtered. The solid collected was washed with ethyl acetate and the filtrate and washings were combined, treated with carbon, filtered through diatomaceous earth, and evaporated, to give a solid (9 g), m.p. 95°–97° C., m/z 244 (M+H). A solution of this solid in a mixture of acetone (100 ml) and pyridine (4 ml) was stirred at reflux for 2.5 hours. The reaction mixture was cooled to 10° C. The solid was collected by filtration and washed with acetone to give 2-bromo-(3-ethyl-4-hydroxyphenyl)ethanone as a solid (10.1 g) with m.p. >260° C.; microanalysis, found: C, 55.8; H, 5.1; N, 4.01; Br, 24.9%; C$_{15}$H$_{19}$BrNO$_2$ requires: C, 55.9; H, 5.0; N, 4.4; Br, 24.8%.

Sodium hydroxide (10 g) was added portionwise to a suspension of the above solid (9.4 g) in water (100 ml). The addition was accompanied by an exotherm which raised the temperature from ambient temperature to 60° C. during the addition. The exotherm was allowed to subside and the reaction mixture was then heated at 90° C., with stirring, for 2.5 hours. The reaction mixture was allowed to cool to ambient temperature, treated with carbon and filtered through diatomaceous earth. The diatomaceous earth was washed with water and the filtrate and washings were combined and acidified to a pH of 1 using concentrated hydrochloric acid. The aqueous solution was extracted with ethyl acetate (3×100 ml). The ethyl acetate extracts were combined, washed with water (100 ml), saturated brine (100 ml), dried (MgSO$_4$) and evaporated. The residue was triturated with 20% ether/n-pentane to give 3-ethyl-4-hydroxybenzoic acid as a solid (3.75 g), m.p. 134°–136° C.; microanalysis, found: C, 64.6; H, 6.0%; C$_9$H$_{10}$O$_3$ requires: C, 65.1; H, 6.1%. NMR: 1.15(3H,t), 2.6(2H,q), 6.9(1H,d), 7.7(2H,m), 10.1(1H,br), 12.3(1H,br).

Thionyl chloride (3 ml) was added dropwise over a period of 2 minutes to ethanol (50 ml) at −10° C. whilst under an atmosphere of argon. The reaction mixture was stirred at −10° C. for 20 minutes and then allowed to warm to ambient temperature. A solution of 3-ethyl-4-hydroxybenzoic acid (3.5 g) in ethanol was added to the reaction mixture dropwise, with cooling (ice-bath). The reaction mixture was allowed to warm to ambient temperature and stirred overnight. The ethanol was removed by evaporation and the residue was partitioned between ethyl acetate (100 ml) and 1M aqueous sodium hydroxide solution (50 ml). The phases were separated and the aqueous phase washed with ethyl acetate (50 ml). The ethyl acetate extracts were combined, washed with water (50 ml) brine (50 ml), dried (MgSO$_4$) and evaporated. The residue, an oil, crystallised on standing to give a solid which was triturated with 10% diethyl ether/ pentane to give ethyl 3-ethyl-4-hydroxybenzoate as a solid (1.4 g), m.p. 73°–74° C.; microanalysis, found: C, 68.4; H, 7.7%; C$_{11}$H$_{14}$O$_3$ requires: C, 68.0; H, 7.3%; NMR: 1.15 (3H,t), 1.3(3H,t), 2.55(2H,q), 4.25(2H,q), 6.85(2H,d), 7.65 (2H,m), 10.15(1H,s).

The above phenol was converted to the triflate using triflic anhydride using the procedure described in Example 30.

EXAMPLE 49

$Y^2$=allyl, $Y^4$=CO$_2$Bu$^t$

Purified by flash column chromatography on silica gel using 15% metanol in dichloromethane containing 1% ammonia (density, 0.88 g/cm$^3$) as eluent to give the title compound as solid, m.p. 104°–106° C.; NMR: 1.2–1.4(1H, m), 1.5–1.7(1H,m), 1.54(9H,s), 1.8–2.02(3H,m), 2.6–2.8 (4H,m), 2.82–2.92(1H,d), 3.05–3.15(1H,d), 3.56(2H,d), 5.00–5.15(2H,m), 5.69(1H,s), 5.86–6.10(1H,m), 7.50(1H,d) and 7.64–7.80(2H,m).

The compound of formula 2 (Z=triflate) was prepared as follows.

Ethyl-3-allyl-4-hydroxybenzoate (1.03 g) was added to a cold solution of sodium hydroxide pellets (0.8 g) in water (10 ml) and the mixture was stirred for 18 hours. 2N aqueous hydrochloric acid was added to acidify the reaction mixture and to give a solid which was extracted into dichloromethane. The organic phase was separated, washed with water, saturated brine and dried (MgSO$_4$). Evaporation gave 3-allyl-4-hydroxybenzoic acid (0.81 g) as a solid, m.p. 119°–123° C.; microanalysis, found C, 66.1; H, 5.9%; C$_{10}$H$_{10}$O$_3$ 0.2H$_2$O requires: C, 66.1; H, 5.77%; NMR (DMSO-d$_6$): 3.31(2H,d), 4.95–5.17(2H,m), 5.85–6.05(1H, m), 6.85(1H,d), 7.55–7.75(2H,m), 10.15(1H,s), 12.30(1H, s); m/z 179(M+H)⁺.

N,N-dimethylformamide di-tert butyl acetal (10 ml) was added over a period of 0.5 hours to a mixture of 3-allyl-4-hydroxybenzoic acid (1.86 g) in toluene (15 ml) at 80° C. and under an atmosphere of argon. The reaction was stirred at 80° C. for 1.25 hours, then cooled to ambient temperature, washed with water and saturated brine and dried (MgSO$_4$). Evaporation gave an oil (2.63 g) which was used without further purification; NMR(CDCl$_3$): 1.58(9H,s), 3.43(2H,d), 5.10–5.25(2H,m), 5.89–6.10(1H,m), 6.79–6.84(1H,m), 7.14–7.20(1H,m), 7.73–7.85(2H,m); m/z 235(M+H).

The triflate of tert-butyl-3-allyl-4-hydroxybenzoate was prepared using triflic anhydride using the method described in Example 29 and purified by flash chromatography on silica gel using 4:1 pentane/ethyl acetate as eluent. NMR (CDCl$_3$): 1.60(9H,s), 3.50(2H,d), 5.03–5.23(2H,m), 5.84–6.01(1H,m), 7.32(1H,d), 7.88–7.98(2H,m); m/z 384 (M+NH$_4$).

EXAMPLE 50

$Y^2$=allyl, $Y^4$=CO$_2$CH$_3$

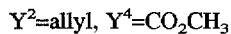

Purified by flash column chromatography on silica gel using 10% methanol in dichloromethane containing 1% ammonia (density, 0.88 g/cm$^3$) as eluent to give the title compound as a solid, m.p. 122–123° C.; NMR: 1.2–1.4(1H, m), 1.5–1.7(1H,m), 1.8–2.02(3H,m), 2.6–2.8(4H,m), 2.82–2.92(1H,d), 3.05–3.15(1H,d), 3.57(2H,d), 3.84(3H,s), 5.02–5.15(2H,m), 5.67(1H,s), 5.86–6.09(1H,m), 7.51(1H,d) and 7.75–7.85(2H,m).

The compound of formula 2 (Z=triflate) was prepared as follows.

A mixture of 4-ethoxycarbonyl-allyloxyphenol (5.15 g), sodium cyanide (123 mg) in methanol (50 ml) was heated at reflux for 18 hours. The reaction mixture was cooled and evaporated. The residue was partitioned between ethyl acetate and water. The organic phase was separated, washed with water, saturated brine, dried (MgSO$_4$) and evaporated to give 4-methoxycarbonyl-allyoxyphenol as an oil (4.7 g); NMR(CDCl$_3$): 3.87(3H,s), 4.55–4.64(2H,m), 5.25–5.48 (2H,m), 5.95–6.16(1H,m), 6.93(2H,d), 7.98(2H,d); m/z 193 (M+H).

The oil was heated at 250°–255° C. for 0.5 hours. The reaction mixture was cooled to ambient temperature to give methyl-3-allyl-4-hydroxy-benzoate (4.4 g) as a solid, m.p. 78°–82° C.; NMR(CDCl$_3$): 3.44(2H,d), 3.88(3H,s), 5.10–5.23(2H,m), 5.61(1H,s), 5.93–6.10(1H,m), 6.84(1H, d), 7.78–7.88(2H,m); m/z 193(M+H).

The triflate of methyl-3-allyl-4-hydroxybenzoate was prepared using triflate anhydride by the method described in Example 29 and purified by flash chromatography on silica gel using 4:1 pentate/ethyl acetate as eluent.

EXAMPLE 51

$Y^2$=H, $Y^4$=NH$_2$

Purified by crystallisation from a mixture of ethyl acetate and hexane to give the title compound as a solid, m.p. 195°–197° C.; NMR: 1.2–1.4(1H,m), 1.5–1.7(1H,m), 1.8–2.02(3H,m), 2.6–2.8(4H,m), 2.82–2.92(1H,d), 3.05–3.15(1H,d), 5.4(3H,s), 6.45–6.55(2H,d) and 7.0–7.1 (2H,d).

The compound used as starting material was prepared as follows.

A mixture of 3-ethynyl-3-hydroxyquinuclidine (750 mg), 4-iodo-trifluoroacetonilide (1.56 g), copper (I) iodide (90 mg), bis(triphenylphosphine)-palladium (II) chloride (175 mg), triethylamine (5 ml) and dimethylformamide (10 ml) was stirred at 80° C. under an atmosphere of argon for 4 hours. The triethylamine and dimethylformamide were removed by evaporation. A saturated aqueous solution of sodium carbonate (20 ml) was then added to the residue and the mixture extracted with dichloromethane (4×20 ml). The organic extracts were combined, dried (MgSO$_4$) and evaporated. The residue was crystallised from acetonitrile to give 3-[2-(4-trifluoroacetamidophenyl)ethynyl]-3-hydroxyquinuclidine as a solid (410 mg) m.p. 222°–223° C.; microanalysis, found: C, 56.9; H, 4.8; N, 7.7%; C$_{17}$H$_{17}$F$_3$N$_2$O$_2$.H$_2$O requires: C, 57.3; H, 5.3; N, 7.8%; NMR: 1.3–1.4(1H,m), 1.65–2.15(4H,m), 3.0–3.6(7H,m), 5.7(1H,s), 7.4–7.5(2H,d), 7.63–7.73(2H,d); m/z 338 (M+H).

The 4-iodotrifluoroacetanilide used as starting material was obtained as follows:

Trifluoroacetic anhydride (2.1 ml) was added dropwise over 15 minutes to a stirred solution of 4-iodo-aniline (2.19 g) in dichloromethane (50 ml) at ambient temperature. The mixture was stirred at ambient temperature for 1 hour. The solvent was removed by evaporation and the residue dried under high vacuum to give 4-iodotrifluoroacetanilide as a solid (3.14 g), m.p. 147°–148° C.; NMR: 7.46–7.55(2H,d), 7.7–7.79(2H,d), 11.3(1H,s); m/z 315(M+H).

EXAMPLE 52

A solution of hydrogen chloride in ethanol was added dropwise to a stirred solution of 3-(4-cyanophenoxymethyl)-3-hydroxyquinuclidine borane complex (0.3 g) in acetone (10 ml) until the solution was pH1. A solid separated and the mixture was stirred for 2 hours at ambient temperature. The solid was collected and washed with ether to give 3-(4-cyanophenoxymethyl)-3-hydroxyquinuclidine hydrochloride (0.3 g) as a colourless solid, m.p. 142°–144° C.; microanalysis, found: C, 61.1; H, 6.8; N, 9.3%; C$_{15}$H$_{18}$N$_2$O$_2$.HCl requires: C, 61.1; H, 6.5; N, 95%; NMR 1.4–1.6(1H,m), 1.6–2.0(2H,m), 2.15–2.3(2H,m), 3.0–3.4 (6H,m), 4.1–4.25(2H,q), 5.4–5.7(1H,br), 7.1–7.2(2H,d), 7.8–7.9(2H,d), 10.6–10.9(1H,br); m/z 259(M+H).

The 3-(4-cyanophenoxymethyl)-3-hydroxyquinuclidine borane complex used as starting material was prepared similarly to 3-(4-acetamido-2-allylphenoxymethyl)-3-hydroxyquinuclidine borane complex in Example 9, except that 4-cyanophenol was used in place of 4-acetamido-2-allylphenol.

EXAMPLES 53–59

Using a procedure similar to that described in Example 52 the following compounds of formula 1, wherein X is —CH$_2$O—, and $Y^2$ and $Y^4$ have the indicated values, were prepared from the corresponding compounds of formula 3, with purification and exceptions as noted. Where the compounds of formula 3 are not commercially available, preparative details are given.

EXAMPLE 53

$Y^2$=H, $Y^4$=CO$_2$Et

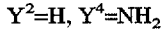

Acetone solution diluted with diethyl ether to give the title compound as its hydrochloride salt, m.p. 160°–162° C.; NMR: 1.3–1.4(3H,t), 1.6–2.0(3H,m), 2.2–2.4(2H,m), 3.0–3.4(6H,m), 4.05–4.2(2H,q), 4.2–4.3(2H,q), 5.6–5.7(1H, s), 7.0–7.2(2H,d), 7.8–8.0(2H,d) and 10.4–10.7(1H,br).

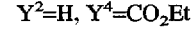

EXAMPLE 54

$Y^2$=H, $Y^4$=CH(CH$_3$)$_2$

Crystallised as its hydrochloride salt, m.p. 194°–196° C.; NMR: 1.1–1.2(6H,d), 1.55–2.0(3H,m), 2.1–2.3(2H,m), 2.7–2.9(1H,m), 2.9–3.4(6H,m), 4.0–4.1(2H,s), 5.5–5.55 (1H,s), 6.9–7.0(2H,d), 7.1–7.2(2H,d) and 10.6–10.9(1H,br).

EXAMPLE 55

$Y^2$=allyl, $Y^4$=CN

Acetone solution diluted with diethyl ether to give the title compound as its hydrochloride salt which was re-crystallised from ethanol to give a solid with m.p. 204°–206° C.; NMR: 1.4–1.9(3H,m), 2.2–2.5(2H,m), 3.0–3.4(6H,m), 3.4–3.5(2H,d), 4.1–4.3(2H,q), 5.0–5.15(2H, m), 5.5–5.7(1H,br), 5.9–6.1(1H,m), 7.1–7.2(1H,d), 7.55–7.6 (1H,s), 7.7–7.75(1H,d) and 10.5–10.7(1H,br).

The compound of formula 3 used as starting material was prepared as described as follows.

A solution of 4-cyanophenol (50 g), allyl bromide (27.2 ml) potassium carbonate (47.8 g) in acetone (100 ml) was heated at reflux for 16 hours. The reaction mixture was evaporated, water was added to the residue and the aqueous mixture was extracted with diethyl ether. The diethyl ether extract was washed with dilute aqueous sodium hydroxide solution, dried (MgSO$_4$) and evaporated to give 4-cyanophenyl allyl ether as a solid, m.p. 41.6° C.; microanalysis, found: C, 75.1; H, 5.8; N, 8.7%; C$_{10}$H$_9$NO$_2$ requires: C, 75.5; H, 5–7; N, 8.8%; NMR: 4.55–4.65(2H,m), 5.2–5.4(2H,m), 5.9–6.05(1H,m), 7.0–7.1(2H,m) and 7.65–7.75(2H,m).

A solution of allyl 4-cyanophenol ether (12 g) in diphenylether (20 ml) was heated at 260° C. for 30 minutes. The reaction mixture was cooled to ambient temperature, diethyl ether was added and the mixture was extracted with 1M aqueous sodium hydroxide solution. The aqueous phase was separated, acidified with 2M aqueous hydrochloric acid solution and extracted with diethyl ether. The organic phase was separated, dried (MgSO$_4$) and evaporated to give 2-allyl-4-cyanophenol as a solid (11.4 g), m.p. 70° C.; microanalysis, found: C, 73.7; H, 5.6; N, 9.2%; C$_{10}$H$_9$NO. 0.25H$_2$O requires: C, 73.4; H, 5.8; N, 8.6%; NMR: 3.2–3.5 (2H,d), 5.0–5.1(2H,m), 5.85–6.05(1H,m), 6.9–7.0(1H,d), 7.4–7.5(2H,m) and 10.6(1H,s).

EXAMPLE 56

$Y^2$=H, $Y^4$=SCH$_3$

Crystallised as its hydrochloride salt, m.p. 147°–149° C.; NMR: 1.55–2.0(3H,m), 2.2–2.3(2H,m), 2.4–2.45(3H,s), 3.0–3.4(6H,m), 3.95–4.1(2H,t), 5.5–5.7(1H,s), 6.9–7.1(2H, d), 7.2–7.4(2H,d) and 10.5–10.8(1H,br).

EXAMPLE 57

$Y^2$=CH=CH—CH$_3$, $Y^2$=CO$_2$Et

Acetone solution diluted with diethyl ether to give the title compound as its hydrochloride salt, m.p. 150°–152° C.; NMR: 1.25–1.4(3H,t), 1.6–1.8(1H,m), 1.8–1.95(5H,m), 2.2–2.4(2H,m), 3.0–3.5(6H,m), 5.4–5.8(1H,br), 6.3–6.5(1H, m), 6.7–6.8(1H,d), 7.1–7.2(1H,d), 7.8–7.9(1H,d), 8.0(1H,s) and 10.7–10.9(1H,s).

The 3-[4-ethoxycarbonyl-2-(1-propenyl)phenoxymethyl] -3-hydroxyquinuclidine borane complex used as starting material was prepared as follows.

Solid potassium carbonate (11.0 g) was added to a solution of 2-allyl-4-ethoxycarbonylphenol (8.2 g) and 3-methylene quinuclidine oxide borane complex (6.1 g) in dry dimethylformamide (65 ml) under an atmosphere of argon. The mixture was stirred for 5 hours at 70° C. The mixture was poured into water (700 ml) and extracted with ethyl acetate (3×250 ml). The ethyl acetate extracts were combined, washed successively with ice-cold aqueous 1M sodium hydroxide solution (3×100 ml) and water (3×100 ml), dried (Na$_2$SO$_4$) and evaporated to a yellow oil (18.4 g), which slowly crystallised. The semi-solid was triturated with ether and the solid was collected by filtration to give 3-(2-allyl-4-ethoxycarbonylphenoxymethyl)-3-hydroxyquinuclidine borane complex as a colourless solid (8.0 g), m.p. 135°–137° C., which contained 10% of the 2-(1-propenyl) isomer.

The ether filtrate was evaporated to give a yellow oil, which on trituration with ether gave 3-[4-ethoxycarbonyl-2-(1-propenyl)phenoxymethyl]-3-hydroxyquinuclidine borane complex as a colourless solid (3.8 g), m.p. 137°–143° C.; NMR(CDCl$_3$): 0.6–2.2(3H, v.br), 1.35–1.4(3H,t), 1.5–1.75(1H,m), 1.75–1.9(2H,m), 1.9–2.0(3H,d), 2.2–2.45 (2H,m), 2.6–2.65(1H,s), 2.8–3.3(6H,m), 3.95–4.0(2H,q), 4.3–4.4(2H,q), 6.2–6.4(1H,m), 6.5–6.65(1H,d), 6.8–6.9(1H, d), 7.85–7.9(1H,d) and 8.1–8.15(1H,s).

EXAMPLE 58

$Y^2$=allyl, $Y^4$=CO$_2$H

Crystallised as its hydrochloride salt, m.p. 232°–234° C.; NMR: 1.6–1.8(1H,m), 1.75–2.0(2H,m), 2.15–2.35(2H,s), 3.0–3.5(8H,m), 4.05–4.25(2H,q), 5.0–5.2(2H,m), 5.5–5.6 (1H,s), 5.9–6.1(1H,m), 7.0–7.1(1H,d), 7.7–7.75(1H,s), 7.75–7.9(1H,d), 10.4–10.7(1H,s) and 12.4–12.7(1H,br).

The 3-(2-allyl-4-carboxyphenoxymethyl)-3-hydroxyquinuclidine borane complex used as starting material was prepared as follows.

Solid potassium carbonate (2.1 g) was added to a solution of 2-allyl-4-ethoxycarbonylphenol (2.7 g) and 3-methylenequinuclidine oxide borane complex (1.5 g) in dry dimethylformamide (10 ml) under an atmosphere of argon. The mixture was stirred for 6 hours at 75° C. The mixture was poured into water (100 ml) and extracted with ethyl acetate (4×70 ml). The ethyl acetate extracts were combined, washed with water (4×50 ml), dried (Na$_2$SO$_4$) and evaporated to afford crude product (4.5 g) which was recrystallised from ethyl acetate to give 3-(2-allyl-4-ethoxycarbonylphenoxymethyl)-3-hydroxyquinuclidine borane complex as a colourless solid (3.0 g), m.p. 143°–145° C. eff.; NMR(CDCl$_3$): 0.6–2.2 (3H,br), 1.35–1.45(3H,t), 1.55–1.75(1H,m), 1.7–1.95(2H,m), 2.2–2.45(2H,m), 2.7–2.75(1H,s), 2.8–3.3(6H,m), 3.35–3.45(2H,d), 3.93–4.13 (2H,q), 4.3–4.45(2H,q), 4.9–5.15(2H,m), 5.85–6.1(1H,m), 6.8–6.9(1H,d), 7.85–7.9(1H,s) and 7.9–8.0(1H,d).

Aqueous 1M sodium hydroxide solution (334 µl) was added to a solution of 3-(2-allyl-4-ethoxycarbonylphenoxymethyl)-3-hydroxyquinuclidine borane complex (0.1 g) in ethanol (2 ml) and water (0.2 ml). The mixture was heated to give a solution which was then heated at reflux for 4 hours. The solution was evaporated and the residue was partitioned with 1:1 ether/ethyl acetate (4 ml) and water (4 ml). The aqueous layer was separated, acidified with aqueous 2M hydrochloric acid (4 drops) to pH3, and extracted with ethyl acetate (2×4 ml). The ethyl acetate extracts were combined, washed with water (1 ml), dried (MgSO$_4$) and evaporated to give 3-(2-allyl-4- carboxyphenoxymethyl)-3-hydroxyquinuclidine borane complex as a colourless foam (0.071 g); NMR: 0.5–2.3(3H, br), 1.3–1.9(3H,m), 2.0–2.25(2H,m), 2.65–3.0(6H,m), 3.35–3.45(2H,d), 3.95–4.15(2H,t), 5.0–5.25(2H,m), 5.85–6.1(1H,m), 7.0–7.1(1H,d), 7.65–7.7(1H,s), 7.7–7.85 (1H,d) and 12.2–12.8(1H,br).

EXAMPLE 59

$Y^2$=allyl, $Y^4$=COCH$_3$

Acetone solution diluted with diethyl ether to give the title compound as its hydrochloride salt, m.p. 154°–156° C.; NMR(CDCl$_3$): 1.7–2.3(3H,m), 2.4–2.6(2H,m), 2.6(3H,s), 3.1–3.6(6H,m), 3.4–3.5(2H,d), 4.0–4.05(1H,s), 4.1–4.4(2H, q), 4.9–5.2(2H,m), 5.9–6.1(1H,m), 6.9–7.0(1H,d), 7.7–7.8 (1H,s), 7.8–7.9(1H,d) and 11.7–12.0(1H,br).

EXAMPLES 60–62

Using a procedure similar to that described in Example 4, the following compounds of formula I, wherein X is —CH$_2$CH$_2$—, and $Y^2$ and $Y^4$ have the indicated values, were prepared from the corresponding compounds of formula 1 in which X is —C≡C—, with purification and exceptions as noted.

EXAMPLE 60

$Y^2$=H, $Y^4$=CO$_2$C(CH$_3$)$_3$

Crystallised from acetonitrile to give the title compound as a solid, m.p. 162°–163° C.; NMR: 1.14–1.34(1H,m), 1.34–1.62(2H,m), 1.54(9H,s), 1.65–1.83(3H,m), 1.87–2.10 (1H,m), 2.45–2.80(8H,m), 4.34(1H,s), 7.32(2H,d) and 7.80 (2H,d). The preparation of the starting material is described in Example 22.

EXAMPLE 61

$Y^2$=H, $Y^4$=O(CH$_2$)$_3$CH$_3$, salt

Hydrogenation of 3-[2-(4-butoxyphenyl)ethynyl]-3-hydroxyquinuclidine hydrochloride (see Example 5) gave the title compound in the form of its hydrochloride salt, which was re-crystallised from acetonitrile to give a solid, m.p. 196°–197° C.; NMR: 0.9–1.0(3H,t), 1.3–1.5(2H,m), 1.6–2.0(8H,m), 2.1–2.3(1H,m), 2.55–2.7(1H,m), 2.9–3.0 (1H,d), 3.05–3.25(6H,m), 3.88–3.97(2H,t), 5.1(1H,s), 6.8–6.88(2H,d) and 7.1–7.18(2H,d).

EXAMPLE 62

A mixture of 3-(2-tri-n-butylethenylstannane)-3-hydroxyquinuclidine (E/Z, 85:15) (0.88 g), ethyl 4-iodobenzoate (1.14 g), tris(dibenzylidine acetone) dipalladium (O) (0.1 g) and cuprous iodide (0.1 g) and anhydrous dimethyl formamide (6 ml) was stirred under an atmosphere of argon. The reaction mixture was heated at 90° C. for 2 hours. The reaction mixture was cooled to ambient temperature, diluted with methylene chloride (150 ml) and washed with 10% aqueous sodium carbonate solution (4×25 ml). The organic extracts were combined, dried (MgSO$_4$), treated with silica-gel (10 g) and evaporated. The residue was purified by column chromatography on silica gel using a 90:10:0.5 (v/v/v) mixture of methylene chloride, methanol and ammonia as eluent to give a residue which was triturated with ethyl acetate to give 3-[2-(4-ethoxycarbonylphenyl) ethenyl]-3-hydroxy quinuclidine (0.154 g) as a solid, m.p. 160°–162° C.; microanalysis, found, C, 66.3; H, 7.2; N, 4.2%; C$_{18}$H$_{23}$NO$_3$ 0.4 CH$_2$Cl$_2$ requires: C, 65.9; H, 7.1; N, 4.2%; NMR(DMSO-d$_6$/CD$_3$CO$_2$D): 1.15(3H,t), 1.4–2.0 (5H,m), 2.8–3.4(6H,m), 4.13(2H,q), 6.63(2H,q), 7.43–7.48 (2H,d) and 7.75–7.79(2H,d); m/z 302(M+H).

The 3-(2-tri-n-butylethenyl stannane)-3-hydroxyquinuclidine used as starting material was obtained as follows.

A mixture of 3-ethynyl-3-hydroxyquinuclidine (0.75 g), tri-n-butyl tin hydride (1.48 ml) and αα'-azo-isobutyronitrile (0.02 g) was heated at 100° C. for 10 minutes. The residue was purified by column chromatography on silica-gel using a 90:10:0.5 (v/v/v) mixture of dichloromethane, methanol and ammonia as eluent to give 3-(2-tri-n-butylethenyl stannane)-3-hydroxyquinuclidine as a solid, m.p. 62°–3° C.; microanalysis, found: C, 56.0; H, 9.7; N, 3.0%; C$_{21}$H$_{41}$NOSn 0.5 CH$_3$OH requires: C, 56.4; H, 9.3 N 3.1%; NMR(DMSO-d$_6$): 0.88(9H,m), 0.8–2.0(23H,m), 2.5–2.9 (6H,m), 4.04(1H,s) and 6.12(2H, m/z 444(M+H).

EXAMPLE 63

A mixture of 3-ethynyl-3-hydroxyquinuclidine (750 mg), 4-n-pentyloxyiodobenzene (1.45 g), bis (triphenylphosphine)-palladium. (II) chloride (175 mg), copper (I) iodide (90 mg), triethylamine (5 ml) and dimethylformamide (10 ml) was stirred at 80° C. under an atmosphere of argon for 4 hours. The mixture was cooled, diluted with water (50 ml) and basified with 2M aqueous sodium hydroxide solution (10 ml). The mixture was extracted with ethyl acetate containing 10% methanol (3×30 ml). The organic extracts were combined, and filtered through a short column of silica gel (Varian Bond—elut S1 silica gel). The eluent was evaporated and the residue was crystallised from acetonitrile to give 3-[2-(4-n-pentyloxyphenyl)ethynyl]-3-hydroxyquinuclidine (950 mg) as a solid, m.p. 153°–154° C.; microanalysis, found: C, 76.4; H, 8.9; N, 4.4%; C$_{20}$H$_{27}$NO$_2$ requires: C, 76.6; H, 8.68; N, 4.47%; NMR: 0.82–0.95(3H,t), 1.22–1.48(5H,m), 1.6–1.76(3H,m), 1.8–2.0(3H,m), 2.6–2.9(6H,m), 3.9–4.0(2H,t), 5.5(1H,s), 6.85–6.95(2H,d), 7.3–7.4(2H,d); m/z 314(M+H).

The 4-n-pentyloxyiodobenzene used as starting material was obtained as follows.

A mixture of 4-iodophenol (6.6 g), 1-bromopentane (4.5 g), anhydrous potassium carbonate (13.8 g) and acetone (100 ml) was stirred at reflux for 24 hours, with the additions of a further quantity of 1-bromopentane after 4 hours (4.5 g) and 8 hours (4.5 g). The acetone was removed by evaporation. The residue was triturated with water (50 ml) and extracted with ether (3×30 ml). The organic extracts were combined, dried (MgSO$_4$) and evaporated. The residue, a colourless oil, was distilled at 160° C. and 0.05 mm pressure (using a Kugelrohr oven) to give 4-n-pentyloxyiodobenzene as a colourless oil (7.8 g); microanalysis, found C, 45.7; H, 5.4%; C$_{11}$H$_{15}$IO requires: C, 45.5; H, 5.2%; NMR(DMSO-d$_6$): 0.84–0.95(3H,t), 1.25–1.48(4H,m), 1.62–1.77(2H,m), 3.88–3.97(2H,t), 6.72–6.8(2H,d), 7.52–7.6(2H,d); m/z 290 (M).

EXAMPLE 64

A mixture of 3-ethenyl-3-hydroxyquinuclidine (1.53 g) 5-(4-iodophenyl)-3-methyl-1,2,4-oxadiazole (2.86 g), bis (triphenylphosphine)-palladium (II) chloride (350 mg), copper (I) iodide (180 mg), triethylamine (7.5 ml) and dimethyl formamide (15 ml) was stirred at 100° C. under an atmosphere of argon for 16 hours. The triethylamine and dimethylformamide were removed by evaporation. The residue was treated with 2M aqueous sodium hydroxide solution (20 ml) and extracted with dichloromethane (3×30 ml). The organic extracts were combined, dried (MgSO$_4$) and evaporated. The residue was purified by flash column chromatography on silica gel using a gradient of 10% methanol in dichloromethane containing 1% ammonia (density, 0.88 g/cm$^3$) to 25% methanol in dichloromethane containing 2% ammonia (density, 0.88 g/cm$^3$) as eluent to give, after further purification by crystallisation from ethanol/n-pentane, 3-[(E)-2-(4-carboxamidophenyl)vinyl]-3-hydroxyquinuclidine (170 mg) as a solid, m.p. 239°–242° C.; microanalysis, found: C, 69.1; H, 7.8; N, 9.9%; C$_{16}$H$_{20}$N$_2$O$_2$.0.25H$_2$O requires: C, 69.4; H, 7.41; N, 10.1%; NMR: 1.2–1.35(1H, m), 1.4–1.55(1H,m), 1.63–1.8(2H,m), 1.95–2.1(1H,m), 2.6–2.85(5H,m), 2.9–3.0(1H,d), 4.85(1H,br), 6.62–6.68(1H, d), 6.72–6.78(1H,d), 7.25(1H,s), 7.47–7.55(2H,d), 7.78–7.86(2H,d), 7.9(1H,s) m/z 273(M+H).

The 5-(4-iodophenyl)-3-methyl-1,2,4-oxadiazole used as starting material was prepared as follows.

Acetamidoxime hydrochloride (1.5 g) was added portionwise to an ice-cooled suspension of sodium hydride (1.18 g of a 60% dispersion in oil) in dry tetrahydrofuran (40 ml) under an atmosphere of argon. Molecular sieves (type 4A, 8–12 mesh) were added to the reaction mixture, followed by a solution of ethyl 4-iodobenzoate (3.73 g) in tetrahydrofuran (10 ml). The reaction mixture was heated at 65° C. for 3 hours. The reaction mixture was allowed to cool to ambient temperature and was then partitioned between ethyl acetate and water. The organic phase was separated, washed with saturated brine, dried (MgSO$_4$) and evaporated. The residue was purified by flash column chromatography on silica gel using a 70:30 (v/v) mixture of ethyl acetate/hexane as eluent to give 3-methyl-5-(4-iodophenyl)-1,2,4-oxadiazole (1.12 g) as a solid, m.p. 136°–137° C.; microanalysis, found: C, 38.2; H, 2.5; N, 9.5%; C$_9$H$_7$IN$_2$O requires: C, 37.8; H, 2.47; N, 9.79%; NMR: 2.41(3H,s), 7.84(2H,d), 8.02(2H,d); m/z 287(M+H).

EXAMPLE 65

A mixture of 3-ethenyl-3-hydroxyquinuclidine (306 mg), tert-butyl-4-iodobenzoate (608 mg), bis(triphenylphosphine)-palladium (II) chloride (70 mg), copper (I) iodide (35 mg), triethylamine (5 ml) and dimethylformamide (10 ml) was stirred at 90° C. under an atmosphere of argon for 6 hours. The mixture was evaporated and the residue was partitioned between aqueous 2M sodium hydroxide solution (12 ml) and dichloromethane (20 ml). The organic layer was separated, washed with water, saturated brine, dried (MgSO$_4$) and evaporated. The residue was purified by flash column chromatography on silica gel using 20% methanol in dichloromethane containing 1% ammonia (density, 0.88 g/cm$^3$) as eluent, followed by recrystallisation from acetonitrile to give 3-[2-(4-tertbutyl benzoate)ethenyl]-3-hydroxy quinuclidine (28 mg) as a solid, m.p. 202°–2.03° C.; microanalysis found: C, 69.2; H, 8.2; N, 3.7%; C$_{20}$H$_{27}$NO$_3$ 1.0 H$_2$O requires: C, 69.1; H 8.4; N, 4.0%; NMR(DMSO-d$^6$): 1.2–1.4(1H,m), 1.54(9H,s), 1.5–1.7(1H,m), 1.8–2.02(3H,m), 2.6–2.8(4H,m), 2.82–2.92 (1H,d), 3.05–3.15(1H,d), 5.16(1H,s), 6.75(2H,s), 7.57(2H, d) and 7.85(2H,d).

EXAMPLE 66

A mixture of 3-(2-allyl-4-ethoxycarbonylphenoxymethyl)-3-hydroxyquinuclidine (0.8 g), palladium-on-charcoal (10% v/v, 0.1 g) and ethanol (40 ml) was stirred under an atmosphere of hydrogen until no further hydrogen uptake occurred. The mixture was filtered and the filtrate was evaporated to a colourless gum. The gum was dissolved in acetone (10 ml) and the solution was treated with a solution of hydrogen chloride in ether to give 3-(4-ethoxycarbonyl-2-propylphenoxymethyl)-3-hydroxyquinuclidine hydrochloride as a colourless solid (1.0 g), m.p. 141°–143° C.; NMR 0.85–0.95(3H,t), 1.25–1.35(3H,t), 1.5–2.0(5H,m), 2.15–2.35(2H,m), 2.55–2.7(2H,t), 3.0–3.4(6H,m), 4.0–4.25 (2H,q), 4.25–4.35(2H,q), 5.5–5.65(1H,br), 7.05–7.1(1H,s), 7.7–7.75(1H,s), 7.75–7.85(1H,d) and 10.6–10.75(1H,br).

EXAMPLE 67

A solution of 3-(4-acetyl-2-allylphenoxymethyl)-3-hydroxyquinuclidine hydrochloride (0.352 g), methoxylamine hydrochloride (0.092 g) and sodium acetate (0.18 g) in water (3 ml) was heated at reflux for 16 hours under an atmosphere of argon.

The solution was partitioned with ethyl acetate (150 ml). The ethyl acetate phase was separated, dried (Na$_2$SO$_4$), and evaporated to an oil. The residue was azeotroped with toluene, (to remove acetic acid,) to give 3-[2-allyl-4-(1-methoxyiminoethyl)phenoxymethyl]-3-hydroxyquinuclidine as a colourless oil (0.27 g); NMR (CDCl$_3$): 1.5–1.8(1H,m), 1.8–2.0(2H,m), 2.2(3H,s), 2.3–2.5 (2H,m), 3.0–3.4(6H,m), 3.4–3.5(2H,d), 4.0(3H,s), 4.0–4.15 (2H,q), 4.9–5.1(2H,m), 5.9–6.1(1H,m), 5.9–6.6(1H,br), 6.8–6.9(1H,d) and 7.4–7.55(2H,m).

EXAMPLE 68

To a solution of 3-[2-(4-ethoxycarbonylphenyl)ethynyl]-3-hydroxyquinuclidine (250 mg) in ethanol (20 ml) was added 4N aqueous sodium hydroxide solution (0.7 ml). The reaction mixture was stirred for 18 hours. The reaction mixture was evaporated and the residue was acidified with 5N hydrochloric acid. The mixture was evaporated to give a solid which was treated with methanol/ethyl acetate to give 3-[2-(4-carboxyphenyl)ethynyl]-3-hydroxyquinuclidine (120 mg), m.p. 288°–290° C.; microanalysis, found: C, 59.4; H, 5.8; N, 4.1; Cl, 13.1%; C$_{16}$H$_{17}$NO$_3$.0.5NaCl. 0.5HCl requires: C, 60.3; H, 5.53; N, 4.39; Cl, 11.1%; NMR: 1.66–1.82(1H,m), 1.86–2.31(4H,m), 3.03–3.45(5H,m), 3.51–3.63(1H,d), 6.55(1H,s), 7.54–7.62(2H,d), 7.89–7.98 (2H,d), 12.1(1H,br); m/z 272(M+H).

The 3-[2-(4-ethoxycarbonylphenyl)ethynyl]-3-hydroxyquinuclidine used as a starting material was prepared as described in Example 8.

EXAMPLE 69

A mixture of 3-[(E)-2-(4-n-butoxyphenyl)vinyl]-3-hydroxyquinuclidine (301 mg), toluene-4-sulphonic acid monohydrate (209 mg) and toluene (20 ml) was stirred at reflux for one hour using a Dean and Stark water separator. The toluene was removed by evaporation and the residue treated with saturated aqueous sodium carbonate solution (10 ml). The mixture was then extracted with ethyl acetate (2×10 ml). The organic extracts were combined, dried (MgSO$_4$) and evaporated to a gum which was purified by flash column chromatography on silica gel using 10% methanol in dichloromethane containing 1% ammonia (density, 0.88 g/cm$^3$) as eluent to give 3-[(E)-2-(4-n-butoxyphenol)vinyl]quinuclidine (240 mg), m.p. 76°–77° C.; microanalysis, found: C, 80.2; H, 8.9; N, 4.7%; C$_{19}$H$_{25}$NO requires: C, 80.5; H, 8.89; N, 4.96%; NMR: 0.88–0.98(3H,t), 1.27–1.51(4H,m), 1.61–1.76(4H,m), 2.38–2.5(2H,m), 2.82–2.96(2H,m), 3.12(1H,br), 3.92–4.0 (2H,t), 6.5(1H,d), 6.62–6.69(1H,d), 6.69–6.76(1H,d), 6.85–6.92(2H,d), 7.38–7.45(2H,d); m/z 284(M+H).

The starting material 3-[(E)-2-(4-n-butoxyphenyl)ethenyl]-3-hydroxyquinuclidine is described in Example 3.

EXAMPLE 70

The procedure described in Example 52 was repeated using 3-(2-allyl-4-isopropoxycarbonylphenoxymethyl)-3-hydroxyquinuclidine borane complex (0.3 g) instead of 3-(4-cyanophenoxymethyl)-3-hydroxyquinuclidine borane complex. The acetone solution was diluted with ether and there was thus obtained 3-(2-allyl-4-isopropoxycarbonylphenoxymethyl)-3-hydroxyquinuclidine hydrochloride as a colourless solid (0.27 g), m.p. 190°–192° C.; microanalysis, found: C, 64.0; H, 8.1; N, 3.5%; $C_{21}H_{29}NO_4 \cdot HCl$ requires: C, 63.7; H, 7.7; N, 3.6; NMR(DMSOd$_6$): 1.25–1.35(6H,d), 1.6–1.95(3H,m), 2.1–2.35(2H,m), 3.0–3.3(6H,m), 3.4–3.5(2H,d), 4.1–4.3 (2H,q), 5.0–5.2(3H,m), 5.55–5.65(1H,s), 5.9–6.1(1H,m), 7.05–7.15(1H,d), 7.7–7.75(1H,s), 7.8–7.9(1H,d) and 10.55–10.75(1H,s); m/z360(M+H).

The 3-(2-allyl-4-isopropoxycarbonylphenoxymethyl)-3-hydroxyquinuclidine borane complex used as starting material was prepared as follows.

2-Allyl-4-isopropoxycarbonylphenol was prepared using the procedure described in Example 55, except that isopropyl 4-hydroxybenzoate was used instead of 4-cyanophenol. There was thus obtained 2-allyl-4-isopropoxycarbonyl phenol as a colourless solid, m.p. 79°–80° C.; microanalysis, found: C, 71.1; H, 7.5%; $C_{13}H_{16}O_3$ requires: C, 70.9; H, 7.3%; NMR(DMSOd$_6$): 1.25–1.3(6H,d), 3.3–3.4(2H,d), 5.0–5.2(3H,m), 5.8–6.1(1H,m), 6.8–7.0(1H,d), 7.6–7.75 (2H,m), and 10.25(1H,s); m/z 221(M+H).

The procedure described in Example 79 was repeated using 2-allyl-4-isopropoxycarbonylphenol (0.44 g) instead of 2-allyl-4-nitrophenol to give 3-(2-allyl-4-isopropoxycarbonylphenoxymethyl)-3-hydroxyquinuclidine borane complex as a solid (0.34 g), m.p. 106°–109° C.; NMR(CDCl$_3$): 0.7–2.2(3H,br), 1.3–1.4 (6H,d), 1.6–1.95(3H,m), 2.2–2.4(2H,m), 2.7–2.75(1H,s), 2.8–3.3(6H,m), 3.4–3.5(2H,d), 3.95–4.1(2H,q), 4.95–5.3 (3H,m), 5.9–6.1(1H,m), 6.8–6.9(1H,d), 7.85–7.9(1H,s) and 9–8.0(1H,d).

EXAMPLE 71

Using the procedure described in Example 5, but using 2,5-dichloroiodobenzene in place of 4-butoxyiodobenzene, there was obtained 3-[2-(2,5-dichlorophenyl)ethynyl]-3-hydroxyquinuclidine which was crystallised from acetonitrile, m.p. 197°–200° C.; NMR: 1.2–1.4(1H,m), 1.5–1.7(1H,m), 1.8–2.02(3H,m), 2.6–2.8(4H,m), 2.82–2.92 (1H,d), 3.05–3.15(1H,d), 6.1(1H,br), 7.4–7.48(1H,d of d), 7.51–7.58(1H,d) and 7.61(1H,d).

EXAMPLE 72

A mixture of (+) 3-ethynyl-3-hydroxyquinuclidine (180 mg), 4-butoxyiodobenzene (330 mg), bis(triphenylphosphine)-palladium (II) chloride (42 mg), copper (I) iodide (21 mg), triethylamine (2.5 ml) and dimethylformamide (5 ml) was stirred under argon at ambient temperature for 4 hours. The triethylamine and dimethylformamide were removed by evaporation. A solution of 2M sodium hydroxide (10 ml) was added and the mixture extracted with dichloromethane (3×10 ml). The combined organic extracts were washed with water (10 ml), dried (MgSO$_4$) and evaporated to a gum. This gum was further purified by flash column chromatography on silica gel using a mixture of 5% methanol in dichloromethane containing 1% ammonia (density, 0.88 g(cm$^3$) as eluent, followed by crystallisation from ethyl acetate to give (+)-3-[2-(4-butoxyphenyl)ethynyl)-3-hydroxyquinuclidine (120 mg) as a solid, m.p. 115°–116° C.; microanalysis, found C, 75.4; H, 8.4; N, 4.5%; $C_{19}H_{25}NO_2$ 0.2H$_2$O requires: C,75.35; H, 8.39, N, 4.63%; NMR: 0.86–0.99(3H,t), 1.2–1.5(3H,m), 1.5–1.71(3H,m), 1.72–1.97(3H,m), 2.6–2.72(4H,m), 2.75–2.85(1H,d), 3.0–3.1(1H,d), 3.9–4.01(2H,t), 5.15(1H, s), 6.85–6.95(2H,d), 7.27–7.37(2H,d); m/z 300(M+H) α=[+26.6]$_{589}$[21] (c=1; methanol).

The (+)-3-ethynyl-3-hydroxyquinuclidine was prepared as follows.

A-solution of (±)-3-ethynyl-3-butyryloxyquinuclidine (4.42 g) in deionised water (700 ml) containing methanol (35 ml) was adjusted to pH 7.0 using an 0.1M aqueous sodium hydroxide solution (dispensed by a pH autotitrater). A suspension of pig liver esterase (8.0 ml, 9200 units,in 3.2M aqueous ammonium sulphate solution at pH8; Sigma Chemical Company Ltd) was added to the reaction mixture and the mixture was stirred at ambient temperature whilst maintaining the pH at 7.0 using 0.1M aqueous sodium hydroxide solution (dispensed by a pH autotitrater). After 5.5 hours, 7.3 ml of the sodium hydroxide solution had been consumed, indicating that the hydrolysis was 35% complete. The pH of the reaction mixture was adjusted to 2.5 using 2M aqueous hydrochloric acid and the mixture was stirred for 10 minutes. 2M aqueous sodium hydroxide solution was then added to the mixture to give a pH of 7.05 and the mixture extracted with diethyl ether (3×200 ml, followed by 12×150 ml). The aqueous phase was separated, and freeze dried over a period of 48 hours to give a solid which was dissolved in deionised water (30 ml). The solution was filtered and the filtrate was basified to pH9 using 10.8M sodium hydroxide solution to give a solid. The solid was collected by filtration to give (+)-3-ethynyl-3-hydroxyquinuclidine, (554 mg), m.p. 204°–207° C., $[\alpha]^{20}_D$=+54.5° (C=0.99, methanol).

The (±)-3-ethynyl-3-butyryloxyquinuclidine used as starting material was prepared as follows.

A solution of n-butyl lithium (100 ml of a 2M solution in pentane) was added portion-wise over a period of 20 minutes to a stirred solution of ethynyltrimethylsilane (19.6 g) in dry tetrahydrofuran (400 ml) at –70° C. The mixture was stirred for 1 hour at –70° C. A solution of 3-quinuclidinone (2.4 g) in dry tetrahydrofuran (100 ml) was then added and the mixture stirred for 1 hour at –70° C. Methanol (1 ml) was then added to the mixture and the mixture allowed to warm to ambient temperature. The solvents were removed by evaporation. Methanol (500 ml) and potassium carbonate (40 g) were added to the residue and the mixture was stirred for 1 hour. The solvent was removed by evaporation. The residue was triturated with water (500 ml) and then dried in vacuo to give 3-ethynyl-3-hydroxy-quinuclidine as a solid, m.p. 193°–197° C.; NMR(DMSO-d$_6$): 1.5–1.3(1H,m), 1.4–1.6(1H,m), 1.7–1.95(3H,m), 2.55–2.8(5H,m), 2.95(1H, d), 3.3(1H,d) and 5.4(1H,s); m/z 152 (M+H).

A mixture of (±)-3-ethynyl-3-hydroxyquinuclidine (15.1 g) and butyric anhydride (60 ml) was stirred at 120° C. for 5 hours. The reaction mixture was cooled to ambient temperature, added to a saturated aqueous solution of sodium carbonate (11) and stirred for 3 hours. The mixture was extracted with diethyl ether (3×100 ml). The diethyl ether extracts were combined, washed with saturated aqueous sodium carbonate solution, dried (MgSO$_4$) and evaporated to give (±)-3-ethynyl-3-butyryloxyquinuclidine as an oil, NMR(200 MHz, DMSOd$_6$): 0.90(3H,t), 1.40(1H,m), 1.57(4H,m), 1.85(1H,m), 2.28(3H,m), 2.66(4H,m), 3.03 (1H,d), 3.18(1H,d) and 3.55(1H,s).

EXAMPLE 73

Using a similar method as described in Example 72, but starting from (−)-3-ethynyl-3-hydroxyquinuclidine (190 mg), there was obtained (−)-3-[2-(4-butoxyphenyl)ethynyl]-3-hydroxyquinuclidine (210 mg), m.p 119°–121° C.; microanalysis, found: C, 75.8; H, 8.5; N, 4.6%; $C_{19}H_{25}NO_2$ requires C,76.2; H, 8.42; N, 4.68Z; m/z 300(M+H), $\alpha=[-24.1]_{589}^{21}$ (C=1, methanol).

The (−)-3-ethynyl-3-hydroxyquinuclidine used as starting material was prepared as follows.

A solution of (±)-3-ethynyl-3-butyryloxy quinuclidine (4.42 g) in deionised water (700 ml) containing methanol (35 ml) was adjusted to pH 7.0 using 0.1M aqueous sodium hydroxide solution (dispensed by a pH autotitrator). A suspension of pig liver esterase (3.0 ml, 3450 units, in 3.2M aqueous ammonium sulphate solution at pH8; Sigma Chemical Company Ltd) was added to the reaction mixture and the mixture stirred at ambient temperature for 46 hours whilst maintaining the pH at 7.0 using 0.1H aqueous sodium hydroxide solution (dispensed from a pH autotitrater). During this period 112.5 ml of the sodium hydroxide solution was consumed, indicating that the hydrolysis was 56% complete. The pH of the reaction mixture was adjusted to 2.52 using 2M aqueous hydrochloric acid and the mixture stirred for 20 minutes. 2M aqueous sodium hydroxide solution was added to the mixture to give a pH of 7.01 and the mixture extracted with diethyl ether (12×150 ml). The diethyl ether extracts were combined, dried ($MgSO_4$) and evaporated to give an oil (2.43 g) containing (−)-3-ethynyl-3-butyryloxyquinuclidine and some butyric acid.

The above oil containing(−)-3-ethynyl-3-butyryloxyquinuclidine was treated rich a solution of potassium hydroxide (2.24 g) in methanol (50 ml). The mixture was stirred at ambient temperature for 2 hours. The mixture was evaporated and deionised water (2 ml) was added to the residue to give a solid. The solid was collected by filtration, washed with water (2×2 ml) and dried under vacuum over phosporus pentoxide to give (−)-3-ethynyl-3-hydroxyquinuclidine (611 mg) as a solid, m.p. 199°–202° C. $[\alpha]^{19}_D=56.1°$ (C=1.02, methanol).

EXAMPLE 74

Fumaric acid (282 mg) was added to a solution of the compound described in Example 5 (598 mg) in ethanol (30 ml), and the mixture was stirred until a complete solution was formed. The ethanol was evaporated and the residue was re-crystallised from acetone to give 3-[2-(4-butoxyphenyl)ethynyl]-3-hydroxyquinuclidine hemifumarate (250 mg), m.p 156°–157° C., microanalysis, found: C, 70.6; H, 7.8; N, 3.8%; $C_{21}H_{27}NO_4$ requires: C, 70.6; H, 7.56; N, 3.92%; NMR: 0.85–0.99(3H,t), 1.3–1.52 (3H,m), 1.57–1.8(3H,m), 1.8–2.05(3H,m), 2.7–2.85(4H,m), 2.85–3.0(1H,d), 3.1–3.25(1H,d), 3.91–4.05(2H,t), 5.6–6.1 (1H,br), 6.5(1H,s), 6.85–6.95(2H,d), 7.3–7.4(2H,d), m/z 300 (M+H).

EXAMPLE 75

Potassium carbonate (0.3 g) was added to a solution of 3-[2-(4-[N-propyl-N-trifluoroacetylamino]phenyl)ethynyl]-3-hydroxy quinuclidine (0.3 g) in methanol (20 ml). The mixture was heated at reflux for 48 hours, cooled to ambient temperature and filtered. The filtrate was evaporated and the residue dissolved in dichloromethane, washed with water, dried ($MgSO_4$) and evaporated. The residue was tritured with acetonitrile to give 3-[2-(4-N-propylaminophenyl) ethynyl]-3-hydroxyquinuclidine as a solid, m.p. 158°–160° C.; NMR: 0.9(3H,t), 1.2–1.4(1H,m), 1.5–1.7(1H,m), 1.55 (2H,m), 1.8–2.02(3H,m), 2.6–2.8(4H,m), 2.82–2.92(1H,d), 3.0(2H,m), 3.05–3.15(1H,d), 5.4(1H,s), 5.95(1H,m), 6.5 (2H,d) and 7.08(2H,d).

The 3-[2-(4-[N-propyl-N-trifluoroacetylamino]phenyl) ethynyl]-3-hydroxy quinuclidine used as starting material was prepared as follows.

Sodium cyanoborohydride (0.63 g) was added to a solution of 4-iodoaniline (2.2 g) and propionaldehyde (0.72 ml) in methanol (15 ml) whilst under an atmosphere of argon. The mixture was stirred at ambient temperature for 72 hours. Sodium cyanoborohydride (0.005 mole) was added and the reaction mixture was stirred for further 48 hours. The pH of the reaction mixture was adjusted to 1 using 2N aqueous hydrocyloric acid. The mixture was filtered and the filtrate was evaporated to yield N-propyl-4-iodoaniline as a solid (1.4 g), NMR: 0.9(3H,t), 1.65(2H,m), 3.1(2H,m), 7.05(2H, d) and 7.67(2H,d).

N-propyl-4-iodoaniline (0.7 g) gas suspended in dichloromethane. Trifluoroacetic anhydride (0.57 ml) was added and the mixture was stirred at ambient temperature for 4 hours. The resulting solution was evaporated to yield N-propyl-N-trifluoroacetyl-4-iodoaniline as an oil (0.8 g), which was used without purification.

Using the procedure described in Example 5 N-propyl-N-trifluoroacethyl-4-iodoaniline was reacted with 3-ethynyl-3-hydroxyquinuclidine to give, after cyrstallisation from acetonitrile 3-[2-(4-[N-propyl-N-trifluoroacetylamino]phenyl)ethnynyl]-3-hydroxy quinuclidine as a solid, m.p. 177°–179° C.; NMR: 0.85(3H,t), 1.2–1.4(1H,m), 1.45(2H,m), 1.5–1.7(1H,m), 1.8–2.02(3H, m), 2.6–2.8(4H,m), 2.82–2.92(1H,d), 3.05–3.15(1H,d), 3.55 (2H,m), 5.09(1H,s), 7.4(2H,d) and 7.5(2H,d).

EXAMPLE 76

The procedure described in Example 5 was repeated using ethyl 4-bromobenzoate in place of 4-butoxyiodobenzene to give 3-[2-(3-ethoxycarbonylphenyl)ethynyl]-3-hydroxy quinuclidine which was purified by flash column chromatography on silica gel using 10% methanol in dichloromethane containing 1% ammonia (density, 0.88 g/cm$^3$) and recrystallised from acetonitrile to give a solid with m.p. 155°–156° C.; NMR: 1.2–1.4(1H,m), 1.33(3H,t), 1.5–1.7(1H,m), 1.8–2.02(3H,m), 2.6–2.8(4H,m), 2.82–2.92(1H,d), 3.05–3.15(1H,d), 4.33(2H,q), 5.65(1H,s), 7.48–7.59(1H,m), 7.64–7.73(1H,m) and 7.89–7.97(2H,m).

EXAMPLE 77

4M aqueous sodium hydroxide solution (0.7 ml) was added to a solution of 3-[2-(4-ethoxycarbonyl-2-propyl phenyl)ethynyl]-3-hydroxyquinuclidine (341 mg) in ethanol (20 ml). The mixture was stirred for 18 hours. The reaction mixture was evaporated, and 2M aqueous hydrochloric acid was added to pH1 and the mixture was evaporated to give a solid. The solid was recrystallised from a mixture of methanol and ethyl acetate to give 3-[2-(4-carboxy-2-propyl phenyl)ethynyl]-3-hydroxyquinuclidine hydrochloride (239 mg) as a solid, m.p. 135°–140° C.; microanalysis, found: C, 63.0; H, 7.7; N, 3.6; Cl, 9.4; $C_{19}H_{23}NO_3$. HCl. 0.75$H_2O$ requires: C, 62.8; H, 7.07; N, 3.85; Cl, 9.76%; NMR: 0.92(3H,t), 1.64(2H, sextet), 1.69–1.85(1H,m), 1.90–2.36 (4H,m), 2.80(2H,t), 3.00–3.50(5H,m), 2.57(1H,d), 3.70–4.34(1H,br.s), 6.58(1H,s), 7.55(1H,d), 7.71–7.89(2H, m); m/z 314(M+H).

The preparation 3-[2-(4-ethoxycarbonyl-2-propylphenyl) ethynyl]-3-hydroxyquinuclidine used as starting material is described in Example 31.

EXAMPLE 78

Using the procedure described in Example 77, but with 3-[2-(allyl-4-ethoxycarbonylphenyl)ethynyl]-3-hydroxyquinuclidine in place of 3-[2-(4-ethoxycarbonyl-2-propyl)ethynyl]-3-hydroxyquinuclidine, there was obtained 3-[2-(2-allyl-4-carboxyphenyl)ethynyl]-3-hydroxyquinuclidine as a foam, NMR: 1.65–1.87(1H,m), 1.88–2.34(4H,m), 3.02–3.65(6H,m), 3.58(2H,d), 5.04–5.18 (2H,m), 5.88–6.11(1H,m), 6.57(1H,s), 7.57(1H,d) and 7.88 (2H,m).

EXAMPLE 79

The procedure described in Example 5 was repeated but using propyl 4-bromo-2-hydroxy benzoate in place of 4-butoxyiodobenzene to give 3-[2-(4-propoxycarbonyl-3-hydroxyphenyl)ethynyl]-3-hydroxy quinuclidine which was crystallised from ethyl acetate to give a solid, m.p. 173°–175° C.; NMR: 0.9(3H,t), 1.2–1.4(1H,m), 1.5–1.7(1H, m), 1.7(2H,m), 1.8–2.02(3H,m), 2.6–2.8(4H,m), 2.82–2.92 (1H,d), 3.05–31.5(1H,d), 4.2(2H,t), 6.95(2H,m) and 7.65 (1H,d).

The propyl 4-bromo-2-hydroxybenzoate was prepared as follows.

Phenyl 4-amino-2-hydroxybenzoate (13.2 g) was suspended in a mixture of 48% hydrobromic acid (15.5 ml) and water (150 ml). The mixture was cooled to 0° C. and a solution of sodium nitrite (4.6 g) in water (5 ml) was added with stirring. The mixture was stirred for 1 hour at 5° C. The mixture was then added, at 40°–50° C., to a solution of copper (I) bromide (6.25 g) in 48% hydrobromic acid (18 ml) and water (9 ml).

The mixture was cooled to ambient temperature and the precipitate was extracted into diethyl ether (200 ml). The ether phase was separated, washed with 2M aqueous hydrochloric acid, brine, dried (MgSO$_2$) and evaporated. The residue was purified by flash column chromatography on silica gel using 10% ethyl acetate in pentane as eluent to give phenyl 4-bromo-2-hydroxy benzoate as a solid (4.5 g); NMR: 7.3(5H,m), 7.5(2H,m), 7.9(1H,d), 10.6(1H,m), m/z293(M+H).

Sodium cyanide was added to a solution of phenyl 4-bromo-2-hydroxybenzoate (1.45 g) in 1-propanol (10 ml). The mixture was heated at reflux for 18 hours. The reaction mixture was cooled to ambient temperature and evaporated. The residue was partitioned between ether and water. The ether phase was separated, dried (MgSO$_4$) and evaporated. The residue was purified by column chromatography on silica gel (Varian Bond Elut S1 silica) using 10% ethyl acetate in pentene as eluent to give n-propyl 4-bromo-2-hydroxybenzoate (1 g), NMR: 1.0(3H,t), 1.72(2H,m), 4.28 (2H,t), 7.15(1H,m), 7.24(1H,m), 7.7(1H,d) and 10.7(1H,s).

EXAMPLE 80

The procedure described in Example 52 was repeated using 3-(2-allyl-4-nitrophenoxymethyl)-3-hydroxyquinuclidine borane complex (0.2 g) instead of 3-(4-cyanophenoxymethyl)-3-hydroxyquinuclidine borane complex. There was thus obtained 3-(2-allyl-4-nitrophenoxymethyl)-3-hydroxyquinuclidine hydrochloride as an off-white solid (0.18 g), m.p. 256°–259° C.; microanalysis, found: C, 57.7; H, 6.6; N, 7.7%; C$_{17}$H$_{22}$N$_2$O$_4$.HCl requires: C, 57.5; H, 6.5; N, 7.9%; NMR: 1.6–1.95(3H,m), 2.1–2.3(2H,m), 3.0–3.4(6H,m), 3.45–3.55 (2H,d), 4.15–4.35(2H,q), 5.05–5.2(2H,m), 5.6(1H,s), 5.9–6.1(1H,m), 7.2–7.25(1H,d), 8.0–8.05(1H,s), 8.1–8.2 (1H,d) and 10.4–10.6(1H,br); m/z 319(M+H).

The 3-(2-allyl-4-nitrophenoxymethyl)-3-hydroxyquinuclidine borane complex used as starting material was prepared as follows.

A stirred solution of 2-allyl-4-nitrophenol (0.42 g), described in Example 30, and 3-methylenequinuclidine oxide borane complex (0.31 g) in dry dimethylformamide (1 ml) was heated at 75° C. under an atmosphere of argon for 44 hours. The red solution was diluted with water (3 ml) and the mixture was extracted with ethyl acetate (3×3 ml). The ethyl acetate extracts were combined, washed with water (4×2.5 ml), dried (Na$_2$SO$_4$) and evaporated. The residual red gum (0.65 g) was purified by chromatography on silica gel (Varian Bond Elut S1 silica), using 20–30% ethyl acetate/ n-pentane as eluent to give 3-(2-allyl-4-nitrophenoxymethyl)-3-hydroxyquinuclidine borane complex as a gum (0.22 g); NMR(CDCl$_3$): 0.5–2.4(3H,br), 1.5–2.0(3H,m), 2.2–2.4(2H,m), 2.6(1H,s), 2.8–3.3(6H,m), 3.4–3.5(2H,d), 4.0–4.2(2H,q), 5.0–5.25(2H,m), 5.9–6.1(1H, m), 6.85–6.95(1H,d) and 8.05–8.2(2H,m).

EXAMPLE 81

A solution of hydrogen chloride in ethanol (4 ml) was added slowly to a stirred solution of 3-(2-allyl-4-ethoxycarbonylphenoxymethyl)-3-hydroxyquinuclidine borane complex (2.7 g) in acetone (40 ml) until the solution was pH1. The colourless solution was stirred for 2 hours at ambient temperature under an atmosphere of argon.

The solution was evaporated. The residual gum was dissolved in aqueous 2M hydrochloric acid (50 ml) and the solution was washed with ethyl acetate (3×50 ml). The organic layer was basified with solid sodium carbonate and the mixture was extracted with ethyl acetate (3×50 ml). The ethyl acetate extracts were combined, dried (Na$_2$SO$_4$) and evaporated. The solid residue was recrystallised from acetone (15 ml) to give 3-(2-allyl-4-ethoxycarbonylphenoxymethyl)-3-hydroxyquinuclidine as a colourless solid (1.8 g), m.p. 143°–145° C.; microanalysis, found: C, 69.2; H, 7.8; N, 4.0%; C$_{20}$H$_{27}$NO$_4$ requires: C, 69.5; H, 7.9; N, 4.1%; NMR(CDCl$_3$): 1.3–1.5(4H,m), 1.5–1.7(2H,m), 2.0–2.2(2H,m), 2.45–2.55(1H,s), 2.6–3.1 (6H,m), 3.3–3.55(2H,m), 3.9–4.2(2H,q), 4.3–4.4(2H,q), 5.0–5.2(2H,m), 5.9–6.1(1H,m), 6.8–6.9(1H,d), 7.9(1H,s), 7.9–8.0(1H,d); m/z 346(M+H).

The 3-(2-allyl-4-ethoxycarbonylphenoxymethyl)-3-hydroxyquinuclidine borane complex used as starting material was prepared from 2-allyl-4-ethoxycarbonylphenol using the procedure which was prepared as follows.

A mixture of ethyl 4-hydroxybenzoate (20 g), potassium carbonate (18.3 g), allylbromide (10.4 ml) and acetone (200 ml) were heated at reflux for 16 hours. The reaction mixture was cooled to ambient temperature, filtered and the filtrate was evaporated. The residue was dissolved in diethyl ether, washed with dilute aqueous sodium hydroxide solution, dried (MgSO$_4$) and evaporated to give ethyl 4-allyloxy benzoate; NMR: 1.25–1.35(3H,t), 4.2–4.35(2H,q), 4.6–4.7 (2H,m), 5.2–5.5(2H,m), 5.96–6.15(1H,m), 7.0–7.1(2H,d), 7.85–7.95(2H,d).

Ethyl 4-allyloxybenzoate (10 g) was heated at 220° C. for 15 minutes. The reaction mixture was cooled to ambient temperature and purified by flash column chromatography on silica gel using a 25:75 (v/v) mixture of ethyl acetate/hexane as eluent to give 2-allyl-4-ethoxycarbonylphenol as a solid (8.87 g), m.p. 67°–70° C.; NMR: 1.25–1.35(3H,t), 3.3–3.45(2H,m), 4.2–4.3(2H,q), 5.0–5.15(2H,m), 5.85–6.05 (1H,m), 6.85–6.9(1H,d), 7.6–7.75(2H,d), 10.2–10.35(1H,s).

EXAMPLE 82

A 1M solution of lithium aluminium hydroxide in tetrahydrofuran (3.0 ml) was added dropwise over 15 minutes to a stirred suspension of 3-[2-(4-bromophenyl)ethynyl]-3-hydroxyquinuclidine (918 mgs) in dry tetrahydrofuran (20 ml) at ambient temperature, under an atmosphere of argon. A complete solution formed as the addition progressed. The mixture was then stirred for 2 days at ambient temperature. A 2.0M solution of sodium hydroxide was then added dropwise to destroy the complex. The mixture was evaporated to dryness and the residue was purified by flash column chromatography on silica gel using 10% methanol in dichloromethane containing 1% ammonia (density, 0.88 g/cm$^3$) to give [3-[2-(4-bromophenyl)-ethenyl]-3-hydroxyquinuclidine which was further purified by crystallisation from ethanol (210 mg) m.p. 218°–219° C.; NMR: 1.25(1H,m), 1.5(1H,m), 1.69(2H,m), 2.0(1H,m), 2.7(5H,m), 2.9(1H,d), 4.8(1H,s), 6.58(1H,d), 6.68(1H,d) and 7.42(4H, m).

EXAMPLE 83

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

|  | mg/tablet |
| --- | --- |
| (a) Tablet I |  |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II |  |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III |  |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule |  |
| Compound Z* | 10 |
| Lactose Ph.Eur. | 488.5 |
| Magnesium stearate | 1.5 |

Note
*The active ingredient Compound Z is a compound of formula I, or a salt thereof, for example a compound of formula I described in any of the preceding Examples.

The tablet compositions (a)–(c) may be enteric coated by conventional means, for example, with cellulose acetate phthalate

SCHEME 1

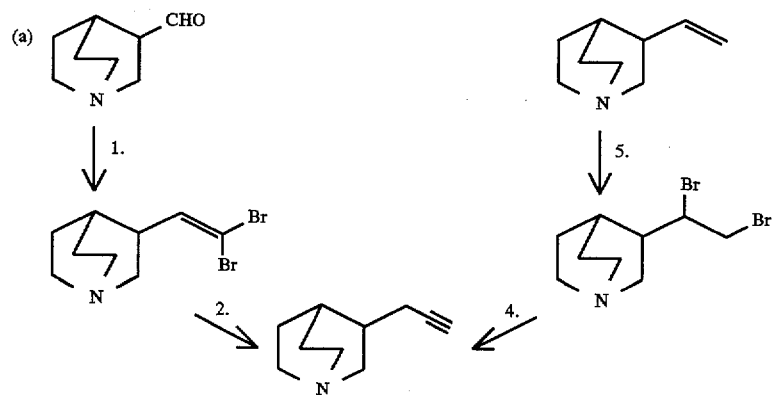

1. CBr$_4$/PPh$_3$/Zn, CH$_2$Cl$_2$, ROOM TEMPERATURE
2. (a) n.BuLi (2 equiv), THF, –60° C., ARGON ATMOSPHERE (b) H$_2$O
3. Br$_2$/H$_2$O
4. t.BuOK, t-BuOH, REFLUX -continued
SCHEME 1

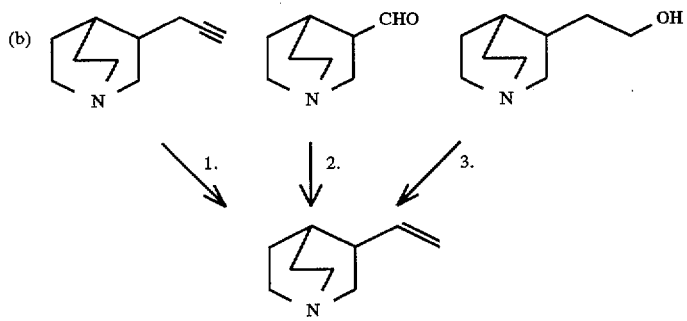

1. H$_2$/Pd. —CaCO$_3$, EtOH
2. Ph$_3$⊕PCH$_3$Br⊖, KOBu$^t$, THF
3. PHTHALIC ANHYDRIDE, BENZENE SULPHONIC ACID, 280° C.

SCHEME 2

(a)

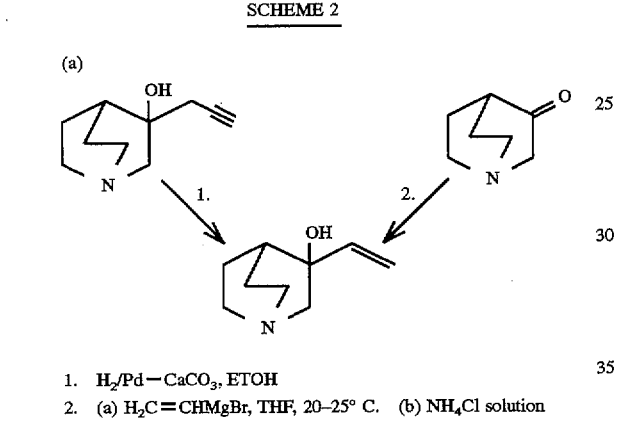

1. H$_2$/Pd—CaCO$_3$, ETOH
2. (a) H$_2$C=CHMgBr, THF, 20–25° C.   (b) NH$_4$Cl solution (b)

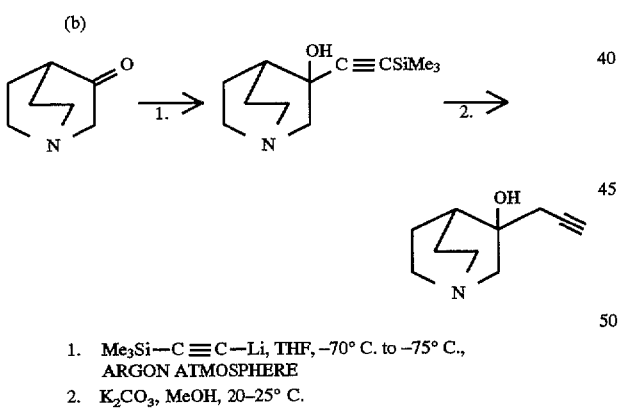

1. Me$_3$Si—C≡C—Li, THF, –70° C. to –75° C., ARGON ATMOSPHERE
2. K$_2$CO$_3$, MeOH, 20–25° C.

CHEMICAL FORMULAE

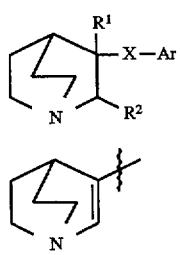 (I)

(Ia)

-continued
CHEMICAL FORMULAE

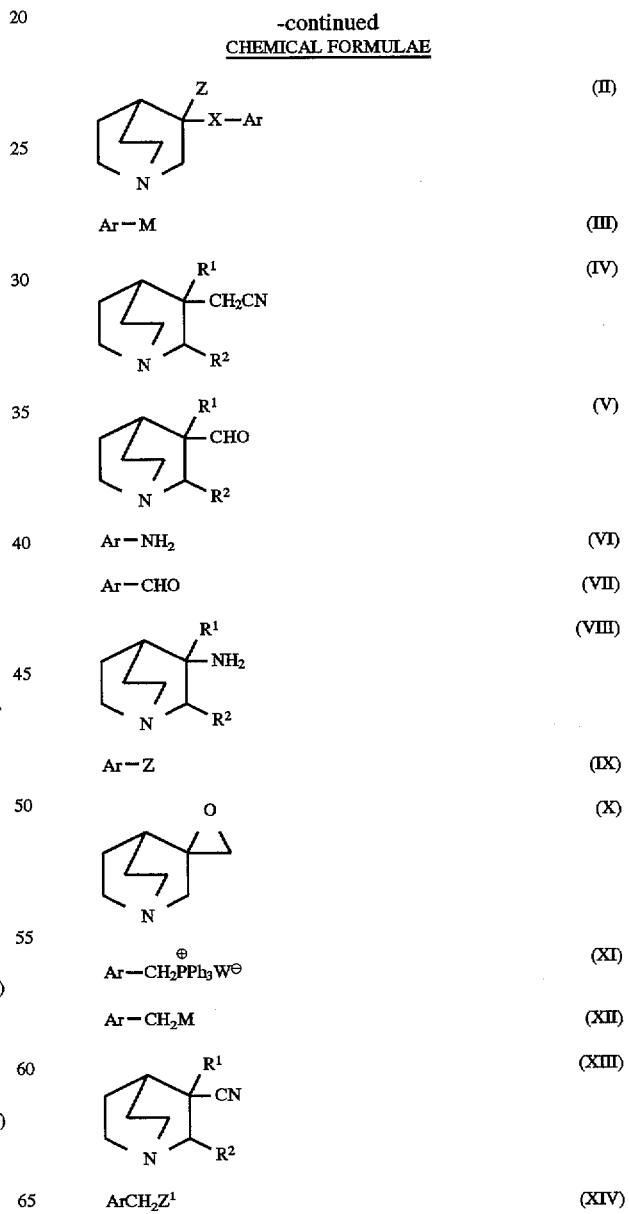

(II)

Ar—M    (III)

(IV)

(V)

Ar—NH$_2$    (VI)

Ar—CHO    (VII)

(VIII)

Ar—Z    (IX)

(X)

Ar—CH$_2$PPh$_3$⊕ W⊖    (XI)

Ar—CH$_2$M    (XII)

(XIII)

ArCH$_2$Z$^1$    (XIV)

-continued
CHEMICAL FORMULAE

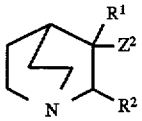 (XV)

ArYH (XVI)

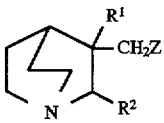 (XVII)

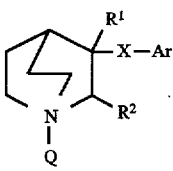 (XVIII)

Ar—C≡CM (XIX)

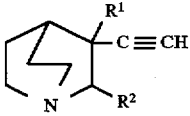 (XX)

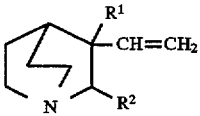 (XXI)

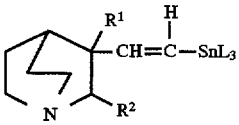 (XXII)

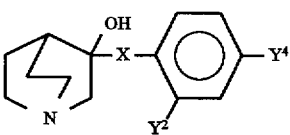 1

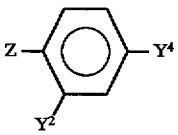 2

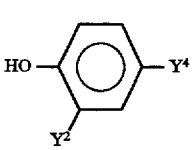 3

We claim:

1. A compound of formula I:

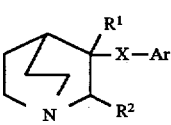 (I)

or a pharmaceutically acceptable salt thereof, wherein:
$R^1$ and $R^2$ are hydrogen, or $R^1$ and $R^2$ are joined together so that $CR^1CR^2$ is a double bond;
X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —CH$_2$S(O)$_n$— and —S(O)$_n$CH$_2$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C) alkylsulphonyl, halogeno(1–6C)alkyl, (1–6C)alkanoylamino, (1–4C)alkylenedioxy, (1–6C)alkanoyl and oxime derivatives thereof and O-(1–6C)alkyl ethers of said oximes; but excluding those compounds in which:

X is —CH$_2$CO— and Ar is phenyl which is unsubstituted or substituted by one or more groups selected from trifluoromethyl, halogeno and (1–6C)alkoxy;

$R^1$ and $R^2$ are hydrogen and X is selected from —CH$_2$O—, —OCH$_2$—, —CH$_2$S(O)$_n$— and —S(O)$_n$CH$_2$—;

$R^1$ and $R^2$ are hydrogen and X is —NHCH$_2$—, and Ar is phenyl substituted by one or more groups selected from (1–6C)alkoxy and halogeno;

$R^1$ and $R^2$ are hydrogen, X is —CH=CH— and Ar is phenyl which is unsubstituted or substituted by one or more halogeno groups;

$R^1$ and $R^2$ are hydrogen, X is —CH$_2$NH— and Ar is unsubstituted phenyl; and $R^1$ and $R^2$ are hydrogen, X is —CH$_2$CH$_2$— and Ar is phenyl which is unsubstituted or substituted by a halogeno, hydroxy, alkyl, alkoxy, amino, cyano, nitro, alkanoylamino carbamoyl, alkylsulphonyl or alkylcarbamoyl substituent.

2. A compound of formula I, or a pharmaceutically acceptable salt thereof; wherein:
$R^1$ is hydroxy and $R^2$ is hydrogen;
X is selected from —CH$_2$CH$_2$—, —CH=CH—, —C≡C—, —CH$_2$O—, —CH$_2$NH—, —CH$_2$CO—, —COCH$_2$—, and —CH$_2$S(O)$_n$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C) alkylsulphonyl, halogeno(1–6C)alkyl, (1–6C)alkanoylamino, (1–4C)alkylenedioxy, (1–6C)alkanoyl and oxime derivatives thereof and O-(1–6C)alkyl ethers of said oximes; but excluding the compounds in which X is —CH$_2$CH$_2$— and Ar is phenyl which is unsubstituted or substituted by a halogeno, hydroxy, alkyl, alkoxy, amino, cyano, nitro, alkanoylamino carbamoyl, alkylsulphonyl or alkylcarbamoyl substituent.

3. A compound as claimed in claim 2 wherein X is selected from —CH$_2$CH$_2$—, —CH=CH—, —C≡C—, —CH$_2$O—, —CH$_2$NH—, and —CH$_2$S—.

4. A compound as claimed in claim 2 wherein X is selected from —CH=CH—, —C≡C—, —CH$_2$O—, —CH$_2$NH—, —CH$_2$CO—, —COCH$_2$—, and CH$_2$S(O)$_n$— wherein n is 0, 1 or 2.

5. A compound as claimed in claim 1 wherein X is —C≡C—.

6. A compound as claimed in claim 1 or 2 wherein Ar is phenyl which optionally bears one or more substituents independently selected from halogeno, amino, nitro, cyano, (1–6C)alkyl, (2–6C)alkenyl, (1–6C)alkoxy, (1–6C) alkylamino, di-[(1–6C)alkyl]amino, (1–6C)alkoxycarbonyl, halogeno(1–6C)alkyl, (1–6C)alkanoylamino, (1–6C) alkanoyl and a group of formula —C(Ra)=NORb in which Ra is (1–6C)alkyl and Rb is (1–6C)alkyl.

7. A compound as claimed in claim 1 wherein R¹ is hydrogen; R² is hydrogen; or R¹ and R² are joined together so that CR¹–CR² is a double bond;

X is selected from —CH₂CH₂—, —CH=CH—, —C≡C—, —CH₂O—, —OCH₂—, —CH₂NH—, —NHCH₂—, —CH₂CO—, —COCH₂—, —CH₂S— and —SCH₂—; and Ar is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C) alkyl, (2–6C)alkenyl, (1–6C)alkoxy, (1–6C) alkylamino, di-[(1–6C)alkyl]amino, N,N-di-[(1–6C) alkyl]carbamoyl, (1–6C)alkoxycarbonyl, (1–6C) alkylthio, (1–6C)alkylsulphinyl, (1–6C) alkylsulphonyl, halogeno (1–6C)alkyl and (1–6C) alkanoylamino.

8. A compound as claimed in claim in any one of claims 1 to 2 wherein X is selected from —CH=CH—, —C≡C— and —CH₂O—.

9. A compound selected from:
3-(4-ethoxycarbonyl-2-allylphenoxymethyl)-3-hydroxyquinuclidine;
3-(2-allyl-4-cyanophenoxymethyl)-3-hydroxyquinuclidine;
3-[2-(4-butoxyphenyl)vinyl]quinuclidine;
3-[2-(4-butoxyphenyl)ethynyl]-3-hydroxyquinuclidine;
3-[2-(4-pentoxyphenyl)ethynyl]-3-hydroxyquinuclidine;
3-[2-(4-pentylphenyl)ethynyl]-3-hydroxyquinuclidine;
3-[2-(4-ethoxycarbonyl-2-allylphenyl)ethynyl]-3-hydroxyquinuclidine; and
3-(2-allyl-4-isopropoxycarbonylphenoxymethyl)-3-hydroxyquinuclidine
and their pharmaceutically acceptable salts.

10. A process for preparing a compound of formula I or a pharmacetically acceptable salt thereof as claimed in claim 1 or 2, which process is selected from:

a) for those compounds in which X is —C≡C— and R¹ is hydrogen or hydroxy and R² is hydrogen, reacting a compound of formula XX:

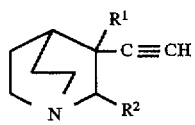

with a compound of formula IX:

Ar—Z (IX)

in which Z is a leaving group in the presence of a catalyst;

b) for those compounds in which X is —C≡C— and R¹ is hydrogen or hydroxy and R² is hydrogen, reacting a compound of formula XXI:

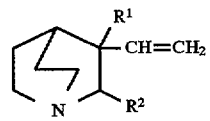

with a compound of formula IX:

Ar—Z (IX)

in which Z is a leaving group in the presence of a catalyst.

11. A pharmaceutical composition which comprises a compound of formula I, or a pharmaceutically acceptable salt thereof, as claimed in any one of claims 1 or 2 together with a pharmaceutically acceptable diluent or carrier.

12. A method for the inhibition of cholesterol biosynthesis in a warm blooded animal in need thereof comprising the administration of a cholesterol biosynthesis inhibiting amount of a compound of formula I:

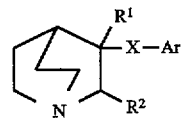

or a pharmaceutically acceptable salt thereof, wherein:
R¹ is hydrogen or hydroxy;
R² is hydrogen;
or R¹ and R² are joined together so that CR¹–CR² is a double bond;

X is selected from —CH₂CH₂—, —CH=CH—, —C≡C—, —CH₂O—, —OCH₂—, —CH₂NH—, —NHCH₂—, —CH₂CO—, —COCH₂—, —CH₂S(O)ₙ— and —S(O)ₙCH₂— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C) alkylsulphonyl, halogeno (1–6C)alkyl, (1–6C) alkanoylamino, (1–4C)alkylenedioxy, (1–6C)alkanoyl and oxime derivatives thereof and O-(1–6C)alkyl ethers of said oximes; provided that when X is selected from —OCH₂—, —NHCH₂—, and —S(O)ₙCH₂—, R¹ is not hydroxy.

13. The method of claim 12 wherein Ar is phenyl which optionally bears one or more substituents independently selected from halogeno, amino, nitro, cyano, (1–6C)alkyl, (2–6C)alkenyl, (1–6C)alkoxy, (1–6C)alkylamino, di-[ (1–6C)alkyl]amino, (1–6C)alkoxycarbonyl, halogeno (1–6C)alkyl, (1–6C)alkanoylamino, (1–6C)alkanoyl and a group of formula —C(Ra)=NORb in which Ra is (1–6C) alkyl and Rb is (1–6C)alkyl.

14. The method of claim 12 or 13 wherein X is selected from —CH₂CH₂—, —CH=CH—, —C≡C—, —CH₂O—, —CH₂NH— and —CH₂S—; and Ar is phenyl which is substituted by one or more substituents independently selected from halogeno, cyano, (1–6C)alkyl, (2–6C)alkenyl, (1–6C)alkoxy, (1–6C)alkoxycarbonyl, halogeno(1–6C) alkyl, (1–6C)alkanoylamino, (1–6C)alkanoyl and a group of formula —C(Ra)=NORb in which Ra is (1–6C)alkyl and Rb is (1–6C)alkyl.

15. A method for the inhibition of cholesterol biosynthesis in a warm blooded animal in need thereof comprising the administration of a cholesterol biosynthesis inhibiting amount of a compound of formula I:

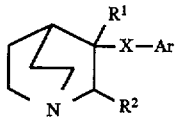
(I)

or a pharmaceutically acceptable salt thereof, wherein:

$R^1$ is hydrogen or hydroxy;

$R^2$ is hydrogen;

or $R^1$ and $R^2$ are joined together so that $CR^1$-$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S$— and —$SCH_2$—; and AR is phenyl which may be optionally unsubstituted or substituted by one or more substituents independently selected from halogeno, hydroxy, amino, nitro, cyano, carboxy, carbamoyl, N-(1–6C)alkylcarbamoyl, (1–6C)alkyl, (2–6C)alkenyl, (1–6C)alkoxy, (1–6C)alkylamino, di-[(1–6C)alkyl]amino, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino; provided that when X is selected from —$OCH_2$—, —$NHCH_2$—, and —$SCH_2$—, $R^1$ is not hydroxy.

16. The method of claim 12 or 13 wherein X is selected from —$CH_2CH_2$—, —CH=CH—, —C≡C— and —$CH_2O$—.

17. The method of claim 12 or 13 wherein $R^1$ is hydroxy and $R^2$ is hydrogen.

18. The method of claim 12, said method further comprising the treatment of hypercholesterolemia or ischaemic disease associated with atheromatous vascular degeneration by said inhibition of cholesterol biosynthesis.

19. A method of inhibiting squalene synthase in a warm blooded animal in need thereof comprising the administration of a squalene synthase inhibiting amount of a compound of formula I:

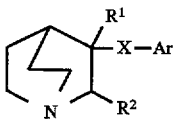
(I)

or a pharmaceutically acceptable salt thereof, wherein:

$R^1$ is hydrogen or hydroxy;

$R^2$ is hydrogen;

or $R^1$ and $R^2$ are joined together so that $CR^1$-$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— wherein n is 0, 1 or 2; and Ar is phenyl which may be optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, (1–4C)alkylenedioxy, (1–6C)alkanoyl and oxime derivatives thereof and O-(1–6C)alkyl ethers of said oximes; provided that when X is selected from —$OCH_2$—, —$NHCH_2$—, and —$S(O)_nCH_2$—, $R^1$ is not hydroxy.

* * * * *